US 9,995,681 B2

(12) United States Patent
Conroy et al.

(10) Patent No.: US 9,995,681 B2
(45) Date of Patent: Jun. 12, 2018

(54) DETERMINING THE QUANTITY OF A TAGGANT IN A LIQUID SAMPLE

(71) Applicant: Authentix, Inc., Addison, TX (US)

(72) Inventors: Jeffrey L. Conroy, Allen, TX (US); Philip B. Forshee, McKinney, TX (US); Paul J. Cronin, Allen, TX (US); Olusola Soyemi, Little Elm, TX (US)

(73) Assignee: Authentix, Inc., Addison, TX (US)

( * ) Notice: Subject to any disclaimer, the term of this patent is extended or adjusted under 35 U.S.C. 154(b) by 0 days. days.

(21) Appl. No.: 14/808,041

(22) Filed: Jul. 24, 2015

(65) Prior Publication Data

US 2015/0355091 A1 Dec. 10, 2015

Related U.S. Application Data

(63) Continuation-in-part of application No. 13/823,333, filed as application No. PCT/US2011/053523 on Sep. 27, 2011.

(60) Provisional application No. 61/387,131, filed on Sep. 28, 2010.

(51) Int. Cl.
*G01N 21/64* (2006.01)
*G01N 33/28* (2006.01)

(52) U.S. Cl.
CPC ....... *G01N 21/643* (2013.01); *G01N 33/2882* (2013.01); *G01N 2021/6439* (2013.01)

(58) Field of Classification Search
CPC .................. G01N 21/6428; G01N 21/643
USPC ........................................ 250/459.1, 458.1
See application file for complete search history.

(56) References Cited

U.S. PATENT DOCUMENTS

| 5,409,666 A | * | 4/1995 | Nagel | A61B 5/1455 |
| | | | | 422/82.05 |
| 5,498,875 A | * | 3/1996 | Obremski | G01J 3/4338 |
| | | | | 250/458.1 |
| 5,525,516 A | | 6/1996 | Krutak et al. | |
| 5,643,728 A | * | 7/1997 | Slater | C12Q 1/6816 |
| | | | | 435/15 |

(Continued)

FOREIGN PATENT DOCUMENTS

| GB | 2497477 A | 6/2013 |
| WO | 2006009810 A1 | 1/2006 |

(Continued)

OTHER PUBLICATIONS

Divya et al., Combining synchronous fluorescence spectroscopy with multivariate methods for the analysis of petrol-kerosene mixtures, 2006,SciencDirect Talanta 72, pp. 43-48.*

(Continued)

*Primary Examiner* — David Porta
*Assistant Examiner* — Djura Malevic
(74) *Attorney, Agent, or Firm* — Conley Rose, P.C.; Rodney B. Carroll

(57) ABSTRACT

Device and methods for detecting/quantifying a fluorescent taggant in a liquid sample. Generally, the liquid samples are fuels having low concentrations (measured in ppb) of a fluorescent taggant. The detection/quantification generates a predicted concentration of the fluorescent tagging compound using a process selected from the group of a multivariate process, a background subtraction process, or a combination of both. The invention addresses the detection of an adulteration of gasoline and diesel fuels.

22 Claims, 19 Drawing Sheets

(56) References Cited

U.S. PATENT DOCUMENTS

| | | | |
|---|---|---|---|
| 5,710,046 A | 1/1998 | Rutledge et al. | |
| 5,723,338 A | 3/1998 | Rutledge et al. | |
| 5,753,511 A * | 5/1998 | Selinfreund | G07F 7/086 |
| | | | 436/172 |
| 5,801,826 A * | 9/1998 | Williams | G01J 3/433 |
| | | | 356/307 |
| 5,804,447 A | 9/1998 | Albert et al. | |
| 5,843,783 A | 12/1998 | Rutledge et al. | |
| 5,928,954 A | 7/1999 | Rutledge et al. | |
| 5,943,129 A | 8/1999 | Hoyt et al. | |
| 5,958,780 A * | 9/1999 | Asher | C10L 1/14 |
| | | | 356/301 |
| 5,980,593 A | 11/1999 | Friswell et al. | |
| 5,984,983 A * | 11/1999 | Asgaonkar | C10L 1/003 |
| | | | 44/385 |
| 5,998,211 A * | 12/1999 | Albert | C10L 1/003 |
| | | | 436/172 |
| 6,124,597 A * | 9/2000 | Shehada | A61B 5/0075 |
| | | | 250/458.1 |
| 6,154,277 A * | 11/2000 | Snelling | G01N 15/0205 |
| | | | 250/575 |
| 6,232,124 B1 * | 5/2001 | Selinfreund | G01N 21/6428 |
| | | | 436/172 |
| 6,251,581 B1 * | 6/2001 | Ullman | C07D 265/30 |
| | | | 252/582 |
| 6,312,958 B1 * | 11/2001 | Meyer | C10L 1/003 |
| | | | 436/139 |
| 6,458,595 B1 * | 10/2002 | Selinfreund | G01N 21/6428 |
| | | | 436/172 |
| 6,490,030 B1 * | 12/2002 | Gill | G01J 3/42 |
| | | | 356/71 |
| 6,525,325 B1 * | 2/2003 | Andrews | G01N 15/0205 |
| | | | 250/301 |
| 6,707,539 B2 * | 3/2004 | Selinfreund | G01J 3/42 |
| | | | 356/71 |
| 7,157,611 B2 | 1/2007 | Banavali et al. | |
| RE39,672 E * | 6/2007 | Shehada | A61B 5/0075 |
| | | | 250/458.1 |
| 7,919,325 B2 * | 4/2011 | Eastwood | G01N 21/6428 |
| | | | 436/172 |
| 9,156,707 B2 * | 10/2015 | Green | C01C 1/086 |
| 2003/0123050 A1 * | 7/2003 | Selinfreund | G01J 3/42 |
| | | | 356/71 |
| 2003/0129758 A1 * | 7/2003 | Smith | C07C 69/017 |
| | | | 436/56 |
| 2003/0154044 A1 * | 8/2003 | Lundstedt | G01N 21/274 |
| | | | 702/104 |
| 2004/0021078 A1 * | 2/2004 | Hagler | G01J 3/02 |
| | | | 250/339.13 |
| 2004/0248307 A1 * | 12/2004 | Grof | G01N 33/2882 |
| | | | 436/56 |
| 2004/0259259 A1 * | 12/2004 | Gill | G01N 21/78 |
| | | | 436/8 |
| 2005/0019939 A1 * | 1/2005 | Spall | G01N 21/359 |
| | | | 436/139 |
| 2005/0275844 A1 | 12/2005 | Kaltenbacher et al. | |
| 2006/0211120 A1 * | 9/2006 | Gill | G01N 21/78 |
| | | | 436/56 |
| 2006/0228802 A1 * | 10/2006 | Tiller | G01N 27/333 |
| | | | 436/56 |
| 2007/0146141 A1 * | 6/2007 | Popplewell | G06K 19/07749 |
| | | | 340/572.8 |
| 2008/0194446 A1 | 8/2008 | Ebert et al. | |
| 2008/0270091 A1 * | 10/2008 | Ramanujam | A61B 5/0059 |
| | | | 703/6 |
| 2009/0006004 A1 | 1/2009 | Sens et al. | |
| 2009/0078860 A1 * | 3/2009 | Kischkat | E21B 49/08 |
| | | | 250/269.1 |
| 2009/0104711 A1 * | 4/2009 | Sim | C09K 11/06 |
| | | | 436/172 |
| 2009/0189086 A1 | 7/2009 | Gessner et al. | |
| 2009/0310127 A1 | 12/2009 | Parks, II et al. | |
| 2009/0319195 A1 * | 12/2009 | Hoots | G01N 21/643 |
| | | | 702/25 |
| 2010/0011656 A1 | 1/2010 | Gessner et al. | |
| 2010/0068714 A1 * | 3/2010 | Van Herpen | G01J 3/02 |
| | | | 435/6.11 |
| 2010/0149531 A1 | 6/2010 | Tang | |
| 2013/0179090 A1 | 7/2013 | Conroy et al. | |

FOREIGN PATENT DOCUMENTS

| | | | |
|---|---|---|---|
| WO | WO2006009810 A1 * | 1/2006 | |
| WO | 2011037894 A1 | 3/2011 | |
| WO | 2012050844 A1 | 4/2012 | |

OTHER PUBLICATIONS

Andrade-Eiroa, Áurea, et al., "Critical approach to synchronous spectrofluorimetry. I,"XP027212971, Trends in Analytical Chemistry, 2010, pp. 885-901, vol. 29, No. 8, Elsevier Ltd.

Bakeev, Katherine A., "Process Analytical Technology: Spectroscopic Tools and Implementation Strategies for the Chemical and Pharmaceutical Industries," Second Edition, 2010, 2 pages of cover and information, John Wiley & Sons, Ltd.

Beebe, Kenneth R., et al., "An Introduction to Multivariate Calibration and Analysis," XP009102134, Analytical Chemistry, Sep. 1, 1987, pp. 1007 A-1017 A, vol. 59, No. 17, American Chemical Society.

Divya, O., et al., "Combining synchronous fluorescence spectroscopy with multivariate methods for the analysis of petrol-kerosene mixtures," XP022343965, Talanta, 2007, pp. 43-48, vol. 72, Elsevier B.V.

Divya, O., et al., "Multivariate methods on the excitation emission matrix fluorescence spectroscopic data of diesel-kerosene mixtures: A Comparative study," XP022209842, Analytica Chimica Acta, 2007, pp. 82-90, vol. 592, Elsevier B.V.

Filing receipt and specification for provisional patent application entitled "Determining the quantity of a taggant in a liquid sample," by Jeffrey L. Conroy, et al., filed on Sep. 28, 2010 as U.S. Appl. No. 61/387,131.

Foreign communication from a priority application—International Search Report and Written Opinion, PCT/US2011/053523, dated Mar. 27, 2012, 18 pages.

Foreign communication from a priority application—International Preliminary Report on Patentability, PCT/US2011/053523, dated Apr. 2, 2013, 11 pages.

Gu, Qun, et al., "Improvement of Inner Filter Effect Correction Based on Determination of Effective Geometric Parameters Using a Conventional Fluorimeter," Anal. Chem., Jan. 1, 2009, pp. 420-426, vol. 81, No. 1, American Chemical Society.

Kessler, R. W., et al., "Multi-Modal-Spectroscopy and Multivariate Data Analysis as a Tool for Non-Invasive Process Analysis," Dresdner Sensor Symposium, 2013, pp. 102-107.

Konstantinov, Konstantin B., et al., "Real-Time Compensation of the Inner Filter Effect in High-Density Bioluminescent Cultures," Biotechnology and Bioengineering, Nov. 20, 1993, pp. 1190-1198, vol. 42, No. 10, John Wiley & Sons, Inc.

Zhao, Wenyi, et al., "Discriminant Analysis of Principal Components for Face Recognition," Apr. 1998, 13 pages.

Office Action (Final) dated Feb. 18, 2016 (31 pages), U.S. Appl. No. 13/823,333, filed Mar. 14, 2013.

Maitra, Saikat, et al., "Principle Component Analysis and Partial Least Squares: Two Dimension Reduction Techniques for Regression," Casualty Actuarial Society, 2008, pp. 79-90.

Office Action dated Sep. 25, 2015 (48 pages), U.S. Appl. No. 13/823,333, filed Mar. 14, 2013.

Foreign communication from a priority application—International Search Report and Written Opinion, PCT/US2016/042560, dated Oct. 26, 2016, 19 pages.

Office Action dated Sep. 12, 2016 (37 pages), U.S. Appl. No. 13/823,333, filed Mar. 14, 2013.

Foreign Communication from a related counterpart application, GB Examination Report dated Sep. 28, 2016 in GB Application No. 1305262.6 (3 pages).

(56) References Cited

OTHER PUBLICATIONS

Adivsory Action dated May 2, 2017 (3 pages), U.S. Appl. No. 13/823,333, filed Mar. 14, 2013.
Office Action dated Jun. 7, 2017 (33 pages), U.S. Appl. No. 13/823,333, filed Mar. 14, 2013.
Final Office Action dated Feb. 24, 2017 (32 pages), U.S. Appl. No. 13/823,333, filed Mar. 14, 2013.
Office Action dated Mar. 8, 2018 (31 pages), U.S. Appl. No. 13/823,333, filed Mar. 14, 2013.
Office Action (Final) dated Oct. 10, 2017 (27 pages), U.S. Appl. No. 13/823,333, filed Mar. 14, 2013.

* cited by examiner

DETERMINING THE QUANTITY OF A TAGGANT IN A LIQUID SAMPLE

CROSS-REFERENCE TO RELATED APPLICATIONS

This application is a continuation-in-part of and claims priority to U.S. patent application Ser. No. 13/823,333 filed on Mar. 14, 2013, published as U.S. Patent Publication US 2013/0179090 A1, which is a filing under 35 U.S.C. 371 of International Application No. PCT/US2011/053523 filed Sep. 27, 2011, entitled "Determining The Quantity Of A Taggant In A Liquid Sample," which claims priority to U.S. Provisional Patent Application No. 61/387,131, filed on Sep. 28, 2010, entitled "Determining The Quantity Of A Taggant In A Liquid Sample," which applications are hereby incorporated herein by reference in their entirety for all purposes.

TECHNICAL FIELD

In general, detecting the adulteration of gasoline and diesel fuels is addressed. More specifically, accurately detecting/quantifying a fluorescence taggant in an unknown and variable fuel matrix is addressed.

BACKGROUND

The variable nature of fuel products renders them a challenging medium for fluorescence-based analysis. Fuels, depending on fuel type and production conditions, exhibit varying ratios of aromatic and aliphatic components. Moreover, the constituents present in fuel tend to change as the result of oxidative reactions that occur over time. Similarly, variability in fuel compositions arise from the addition of oxygenates (e.g., ethanol, MTBE, and the like) or biologically derived components such as biodiesel.

Changes in fluorescence absorbance and emission bands result from fluctuations in the structure of the solvation shell around a fluorophore. Moreover, spectral shifts (both bathochromic and hypsochromic) in the absorption and emission bands are often induced by a change in solvent mixture or composition; these shifts commonly referred to as solvatochromic shifts, are experimental evidence of changes in the solvation energy. In other words, when a fluorophore is surrounded by solvent molecules, its ground state and excited state are more or less stabilized by fluorophore-solvent interactions, depending on the chemical nature of both the fluorophore and solvent molecules.

Similarly, the fluorescence quantum yield (the ratio of the number of photons emitted to the number of photons absorbed by the fluorophore) is dependent on the solvent in which the analysis is conducted. A variety of non-radiative de-excitation pathways are available and impact the fluorescence efficiency through mechanisms of dynamic or static quenching. Additionally, the temperature of a sample at the time of measurement has an impact on the fluorescence intensity observed for a given quantity of a fluorophore in solution. Generally, an increase in temperature results in a decrease in the fluorescence quantum yield because of an increase in the non-radiative processes related to collisions with solvent molecules, intramolecular vibrations, and rotations.

An additional problem presented when analyzing for a fluorescent taggant in fuels is that of a native variable fluorescence background. Fuels, based on production conditions, chemical composition of starting crude oil, and age of the fuels at the time of analysis, exhibit a natural fluorescence background. This background fluorescence is highly variable and further complicates the quantification of a fluorescent taggant.

An additional problem encountered is the presence of colorants often added to fuels. It is fairly common throughout the world to add visible dyes to fuels; this practice is often employed to allow specific grades or brands of fuel to be visually identified by consumers. The absorption or emission of these dyes can impinge in the spectral response range of a fluorescent taggant, further complicating identification/quantification.

These effects and compositional differences have a dramatic impact on the ability to accurately quantify the amount of a fluorophore present in a fuel of unknown pedigree.

SUMMARY

The present invention relates to devices and methods for determining the quantity of a taggant in a liquid sample. Aspects and embodiments of the invention are set forth in the claims.

In general, in one aspect, the invention features a method for determining whether a liquid sample includes a particular fluorescent tagging compound at a preset concentration. The method includes obtaining a measured emission spectrum from the liquid sample in which the liquid sample is exposed to a light source that causes the particular fluorescent tagging compound to fluoresce over a spectral range. The method further includes generating a predicted concentration of the particular fluorescent tagging compound in the liquid sample. The generating includes a multivariate process, a background subtraction process, or both. The method further includes comparing the predicted concentration of the particular fluorescent tagging compound in the liquid sample with the preset concentration of the particular fluorescent tagging compound in the liquid sample.

With respect to the multivariate process utilized in this method, the multivariate process includes selecting a library that includes a plurality of known emission spectra. Each of the plurality of known emission spectra is correlated to a known concentration of the particular fluorescent tagging compound. The multivariate process further includes utilizing the library and the measured emission spectrum to generate the predicted concentration of the particular fluorescent tagging compound in the liquid sample.

With respect to the background subtraction process utilized in this method, the background subtraction process includes determining a background emission spectrum from the measured emission spectrum. The background subtraction process further includes eliminating the background emission spectrum from the measured emission spectrum to obtain a predicted emission spectrum. The background subtraction process further includes evaluating the predicted emission spectrum to generate the predicted concentration of the particular fluorescent tagging compound in the liquid sample.

Implementations of the invention can include one or more of the following features:

The liquid sample can be determined to include the particular fluorescent tagging compound at the preset concentration when the predicted concentration is within a present range of the particular fluorescent tagging compound in the liquid sample. The liquid sample can be determined not to comprise the particular fluorescent tagging compound at the preset concentration when the predicted concentration is outside the present range of the particular fluorescent tagging compound in the liquid sample.

The method can further include authenticating the liquid sample. The liquid sample can be determined to be authentic when the predicted concentration is within a preset percentage of the preset concentration of the particular fluorescent tagging compound in the liquid sample. The liquid sample can be determined to not be authentic when the predicted concentration is outside the preset percentage of the preset concentration of the particular fluorescent tagging compound in the liquid sample.

In general, in another aspect, the invention features a device for determining the presence of a particular fluorescent tagging compound in a liquid sample. The device includes a light source, a liquid sample container, an optical detector, and a signal processing module. The liquid sample container is operable for receiving the liquid sample. The light source is operable for providing excitation light on the liquid sample in the liquid sample container whereby the liquid sample may fluoresce and emit an emission spectrum. The optical detector is operable for measuring the emission spectrum emitted from the liquid sample. The signal processing module is operably connected to the optical detector to obtain the measured emission spectrum of the liquid sample from the optical detector. The signal processing module includes a memory unit for storing a computer program for operating the device and a processor coupled to the memory unit. The processor, responsive to the computer program, is programmed to generate a predicted concentration of particular fluorescent tagging compound in the liquid sample. The generating includes a multivariate process, a background subtraction process, or both.

With respect to the multivariate process utilized in this method, the multivariate process includes selecting a library that includes a plurality of known emission spectra. Each of the plurality of known emission spectra is correlated to a known concentration of the particular fluorescent tagging compound. The multivariate process further includes utilizing the library and the measured emission spectrum to generate the predicted concentration of the particular fluorescent tagging compound in the liquid sample.

With respect to the background subtraction process utilized in this method, the background subtraction process includes determining a background emission spectrum from the measured emission spectrum. The background subtraction process further includes eliminating the background emission spectrum from the measured emission spectrum to obtain a predicted emission spectrum. The background subtraction process further includes evaluating the predicted emission spectrum to generate the predicted concentration of the particular fluorescent tagging compound in the liquid sample.

Implementations of the invention can include one or more of the following features:

The processor, responsive to the computer program, can be programmed to compare the predicted concentration of the particular fluorescent tagging compound in the liquid sample with a preset concentration of the particular fluorescent tagging compound in the liquid sample.

The processor, responsive to the computer program, can be programmed to determine whether the liquid sample includes the particular fluorescent tagging compound at the preset concentration. The liquid sample can be determined to include the particular fluorescent tagging compound at the preset concentration when the predicted concentration is within a present range of the particular fluorescent tagging compound in the liquid sample. The liquid sample can be determined not to include the particular fluorescent tagging compound at the preset concentration when the predicted concentration is outside the present range of the particular fluorescent tagging compound in the liquid sample.

The processor, responsive to the computer program, can be programmed to authenticate the liquid sample. The liquid sample can be determined to be authentic when the predicted concentration is within a preset range of the preset concentration of the particular fluorescent tagging compound in the liquid sample. The liquid sample can be determined to not be authentic when the predicted concentration is outside the preset range of the preset concentration of the particular fluorescent tagging compound in the liquid sample.

Implementations of the method and/or device of the invention can also include one or more of the following features:

The particular fluorescent tagging compound can be a first particular fluorescent tagging agent.

The particular fluorescent tagging compound can be a combination of (i) a first particular fluorescent tagging agent and (ii) a second particular tagging agent. The preset concentration can be (i) a first preset concentration of the first particular fluorescent tagging agent and (ii) a second preset concentration of the second particular fluorescent tagging agent.

The predicted concentration of the particular fluorescent tagging compound in the liquid sample can include (i) a first predicted concentration of the first particular fluorescent tagging agent and (ii) a second predicted concentration of the second particular fluorescent agent.

The present range of the particular fluorescent tagging compound in the liquid sample can include (i) a first present range of the first particular fluorescent tagging agent and (ii) a second present range of the first particular fluorescent tagging agent.

The particular fluorescent tagging compound can be a combination of three or more particular fluorescent tagging agents. The preset concentration can be a preset concentration for each of the three or more particular fluorescent tagging agents. The predicted concentration of the particular fluorescent tagging compound in the liquid sample can include a predicted concentration for each of the three or more particular fluorescent tagging agents. The present range of the particular fluorescent tagging compound in the liquid sample can include a present range for each of the three or more particular fluorescent tagging agents.

The generating can include the multivariate process.

The generating can include the background subtraction process.

The particular fluorescent tagging compound can include a first particular fluorescent tagging agent having an emission fluorescence in a range of from about 500 nm to about 900 nm.

The particular fluorescent tagging compound can include a second particular fluorescent tagging agent. The second particular fluorescent tagging agent can have an emission fluorescence in a range of from about 500 nm to about 900 nm. The first particular fluorescent tagging agent and the second particular fluorescent tagging agent can have different emission fluorescence in a range of from about 500 nm to about 900 nm.

The particular fluorescent tagging compound can include a third particular fluorescent tagging agent. The third particular fluorescent tagging agent can have an emission fluorescence in a range of from about 500 nm to about 900 nm. The first particular fluorescent tagging agent, the second particular fluorescent tagging agent, and the third particular fluorescent tagging agent can have different emission fluorescence in a range of from about 500 nm to about 900 nm.

The spectral range can include a range of from 600 nm to 800 nm.

The spectral range can include a range of from 500 nm to 900 nm.

The liquid can be a liquid petroleum hydrocarbon-based fuel, a biologically-derived fuel (biofuel), or a common industrial solvent.

The liquid sample can include a known type of liquid. The utilizing the library can include utilizing only the measured emission spectrum measured from the known type of liquid in the library.

The liquid sample can be from a known geographical region. The utilizing the library can include utilizing only the measured emission spectrum measured from that known geographical region.

Utilizing the library and the measured emission spectrum to generate the predicted concentration of the particular fluorescent tagging compound in the liquid sample can include performing a multivariate analysis utilizing the library and the measured emission spectrum.

The processor, responsive to the computer program, can be programmed to utilize the library and the measured emission spectra to generate the predicted concentration of the particular fluorescent tagging compound in the liquid sample by performing a multivariate analysis utilizing the library and the measured emission spectra.

The multivariate analysis can include a partial least squares analysis.

The multivariate analysis can include a principal components regression analysis.

The multivariate analysis can yield a calibration model that includes a plurality of spectral vectors correlation scores relating to concentration of the particular fluorescent tagging compound.

The utilizing the library and the measured emission spectrum to generate the predicted concentration of the particular fluorescent tagging compound in the liquid sample can further include using the calibration model to calculate the predicted concentration of the particular fluorescent tagging compound in the liquid sample.

The determining the background emission spectrum can include obtaining at least three data points from the measured emission spectrum and using these three data points to calculate the background emission spectrum.

The calculating the background emission spectrum can include fitting the three data points into a quadratic curve.

The calculating the background emission spectrum can include fitting the three data points into an exponential curve.

The calculating the background emission spectrum can include fitting the three data points into a linear combination of an exponential curve and a quadratic curve.

The eliminating the background spectrum from the measured emission spectrum can include subtracting the background spectrum from the measured emission spectrum.

The evaluating the predicted emission spectrum to determine a predicted concentration of the particular fluorescent tagging compound in the liquid sample can include calculating the area under the predicted emission spectrum.

The evaluating the predicted emission spectrum to determine a predicted concentration of the particular fluorescent tagging compound in the liquid sample can include evaluating at least one peak of the predicted emission spectrum.

The processor, responsive to the computer program, can be programmed to perform the multivariate analysis that yields a calibration model that includes a plurality of spectral vectors correlation scores relating to concentration of the particular fluorescent tagging compound.

The processor, responsive to the computer program, can be programmed to utilize the library and the measured emission spectrum to generate the predicted concentration of the particular fluorescent tagging compound in the liquid sample by further using the calibration model to calculate the predicted concentration of the particular fluorescent tagging compound in the liquid sample.

The processor, responsive to the computer program, can be programmed to determine the background emission spectrum by obtaining at least three data points from the measured emission spectra and using these three data points to calculate the background emission spectrum.

The processor, responsive to the computer program, can be programmed to calculate the background emission spectra by fitting the three data points into a quadratic curve.

The processor, responsive to the computer program, can be programmed to calculate the background emission spectra by fitting the three data points into an exponential curve.

The processor, responsive to the computer program, can be programmed to calculate the background emission spectra by fitting the three data points into a linear combination of an exponential curve and a quadratic curve.

The processor, responsive to the computer program, can be programmed to eliminate the background spectrum from the measured emission spectrum by subtracting the background spectrum from the measured emission spectrum.

The processor, responsive to the computer program, can be programmed to evaluate the predicted emission spectrum to generate the predicted concentration of the particular fluorescent tagging compound in the liquid sample by calculating the area under the predicted emission spectrum.

The processor, responsive to the computer program, can be programmed to evaluate the predicted emission spectrum to generate the predicted concentration of the particular fluorescent tagging compound in the liquid sample by evaluating at least one peak of the predicted emission spectrum.

The preset range of the concentration of the preset concentration can be within 10% of the preset concentration.

The present range of each of the particular fluorescent tagging agents can be within 10% of each of the respective present concentrations of the particular fluorescent tagging agents.

The preset range of the concentration of the preset concentration can be within 5% of the preset concentration.

The present range of each of the particular fluorescent tagging agents can be within 5% of each of the respective present concentrations of the particular fluorescent tagging agents.

The present range of the concentration of the preset concentration can be within 5 ppb of the preset concentration.

The present range of each of the particular fluorescent tagging agents can be within 5 ppb of each of the respective present concentrations of the particular fluorescent tagging agents.

The present range of the concentration of the preset concentration can be within 1 ppb of the preset concentration.

The present range of each of the particular fluorescent tagging agents can be within 1 ppb of each of the respective present concentrations of the particular fluorescent tagging agents.

The present range of each of the particular fluorescent tagging agents can be within 1 ppb of each of the respective present concentrations of the particular fluorescent tagging agents.

Obtaining the measured emission spectrum from the liquid sample can include measuring the emission spectrum of the liquid sample using an optical detector.

Obtaining a measured emission spectrum from the liquid sample can include regulating the temperature of at least one of the optical detector, the light source, and the liquid sample.

The device further includes a temperature regulator operatively connected to at least one of the optical detector, the light source, and the liquid sample.

The preset concentration of the particular fluorescent tagging compound in the liquid sample can be at most about 1000 ppb.

The preset concentration of each of the particular fluorescent tagging agents in the liquid sample can be at most about 1000 ppb.

The preset concentration of the particular fluorescent tagging compound in the liquid sample can be at most about 100 ppb.

The preset concentration of each of the particular fluorescent tagging agents in the liquid sample can be at most about 100 ppb.

The preset concentration of the particular fluorescent tagging compound in the liquid sample can be between about 5 ppb and about 50 ppb.

The preset concentration of each of the particular fluorescent tagging agents in the liquid sample can be at most about 5 ppb and about 50 ppb.

The preset concentration of the particular fluorescent tagging compound in the liquid sample can be between about 10 ppb and about 25 ppb.

The preset concentration of each of the particular fluorescent tagging agents in the liquid sample can be at most about 10 ppb and about 25 ppb.

The preset concentration of the particular fluorescent tagging compound in the liquid sample can be 0 ppb.

The processor, responsive to the computer program, can be programmed to determine whether the predicted concentration is within 1 ppb of the preset concentration of the particular fluorescent tagging compound in the liquid sample. The processor, responsive to the computer program, can be programmed to determine whether the predicted concentration is more than 1 ppb of the preset concentration of the particular fluorescent tagging compound in the liquid sample.

These and other features will be more clearly understood from the following detailed description taken in conjunction with the accompanying drawings and claims.

DETAILED DESCRIPTION

It should be understood at the outset that although an illustrative implementation of one or more embodiments are provided below, the disclosed systems and/or methods may be implemented using any number of techniques, whether currently known or in existence. The disclosure should in no way be limited to the illustrative implementations, drawings, and techniques illustrated below, including the exemplary designs and implementations illustrated and described herein, but may be modified within the scope of the appended claims along with their full scope of equivalents.

Embodiments of the present invention provide a device, e.g., a portable device, capable of an accurate determination of a fluorescent taggant added to a liquid sample, as well as methods capable of being employed on said device for more accurately quantifying the concentration of a fluorescent taggant in an unknown liquid sample matrix. In the following description, liquid fuel serves as an illustrative liquid sample, but it will be understood that the following description is equally applicable to other liquids, e.g., to alternative hydrocarbon-based (e.g., hydrocarbon) liquids.

In regards to embodiments of the present invention disclosed herein, there is great flexibility with respect to the fluorescent taggants that can be advantageously detected by the disclosed devices and methods. Though specific ones may be disclosed herein, any inorganic, organic, or metal complex structures that generate fluorescence emissions in a wavelength range of 600-1000 nm may be used, e.g., in a range of about 500 nm to about 900 nm. These include, but are not limited to, phthalocyanines, naphthalocyanines, polymethine dyes, dibenzanthrones, isobenzanthrones, aza-dipyrromethenes, dipyrromethenes, rylenes, squaric acid dyes, rhodamines, oxazines, and coumarins. Some examples of compatible florescence structures for the disclosed detection methods can be found in the following patents and applications: U.S. Pat. Nos. 5,525,516, 5,804,447, 5,710,046, 5,723,338, 5,843,783, 5,928,954, and 7,157,611, U.S. Patent Publication Nos. 2005/0019939, 2008/0194446, 2009/0189086, and 2010/0011656, and PCT Patent Application No. WO 2011/037894, all of which are hereby incorporated by reference herein.

Figure 1:
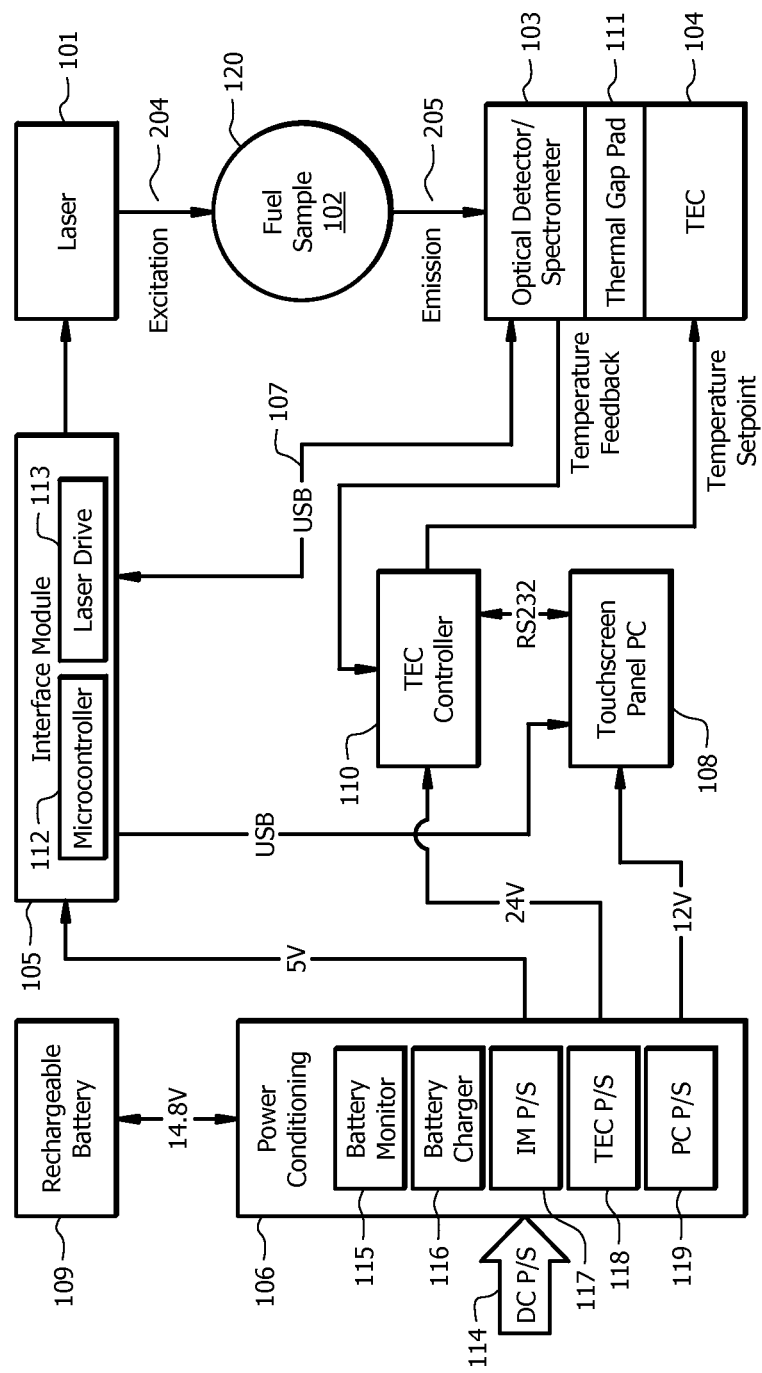
FIG. 1 illustrates a block diagram of an embodiment of a fluorescence spectrometer in accordance with the present invention.

Referring to FIG. 1, such an optionally portable device 100 may include (i) a light source 101 (e.g., a laser or light emitting diode) for excitation of a liquid sample 102, (ii) an optical detector operable for measuring the emission spectra emitted from the liquid sample, e.g., a charge coupled device-based optical detector and spectrometer 103, (iii) an optional temperature regulator, e.g., cooling/heating device 104 (e.g., a thermoelectric cooler (TEC)) configured to regulate (operably connected to) the temperature of at least one of, e.g., all of, the optical detector 103, light source 101, and sample 102, and (iv) signal processing module 105 and typically power control modules 106 coupled to the light source 101, optical detector 103, and, when present, temperature regulator 104. The liquid sample 102 may be a liquid fuel sample. The sample 102 is positioned inside a container 120 (such as a vial). The container 120 can be a disposable vial that can be removed from the portable device 100 and replaced with another vial.

Figure 2:
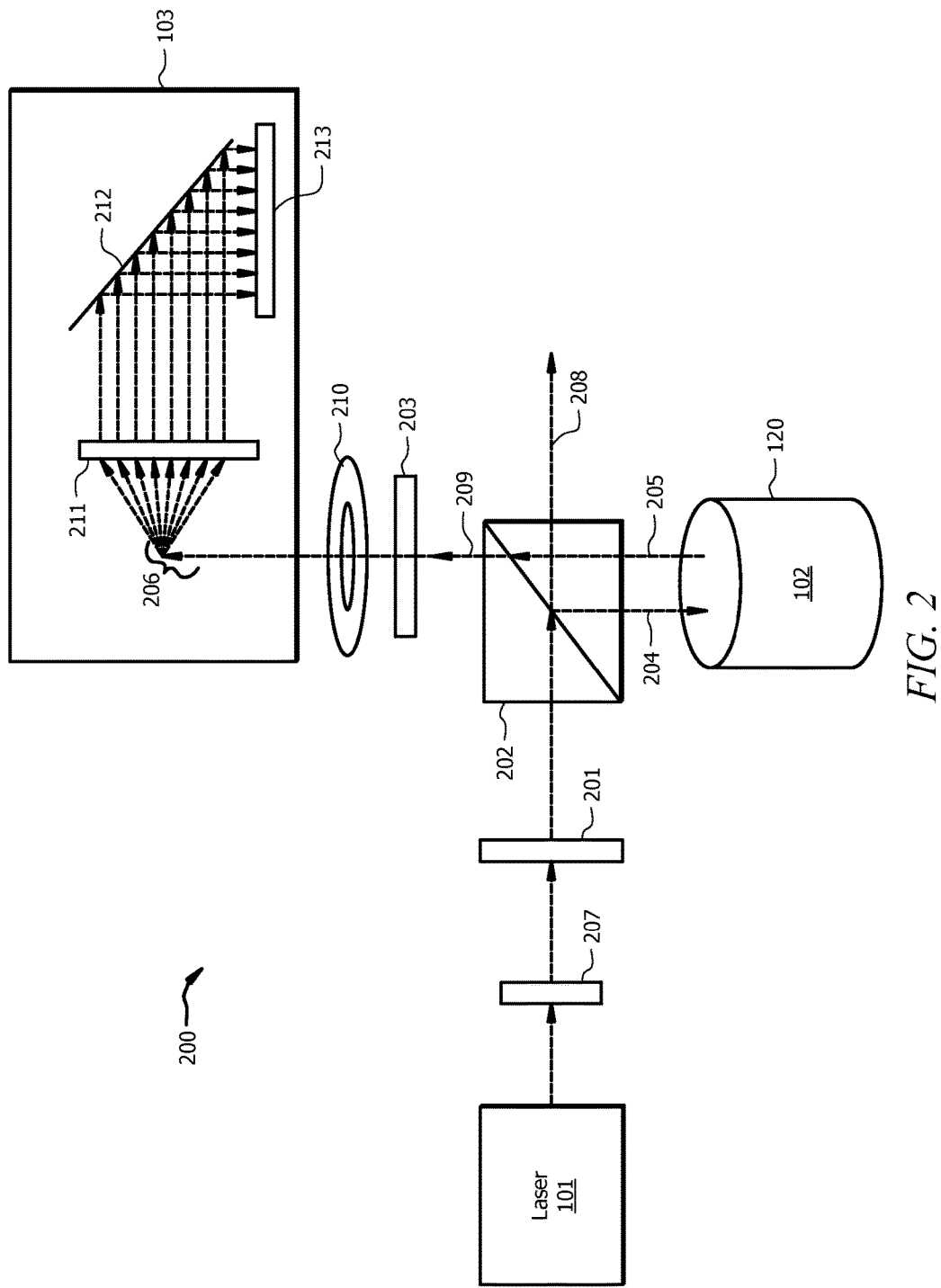
FIG. 2 illustrates a diagram of optical elements that can be used in the fluorescence spectrometer illustrated in FIG. 1.
Figure 3A:
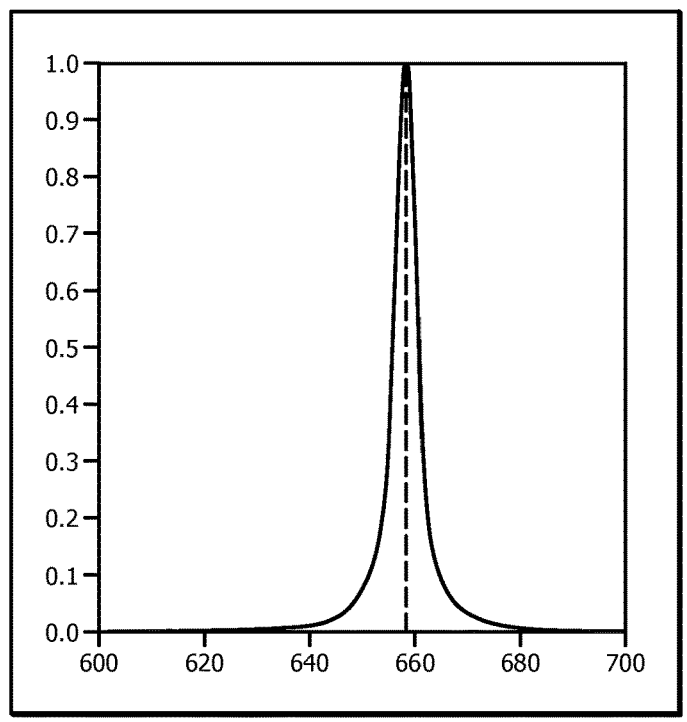
FIG. 3A illustrates an example of a spectrum of light that can be emitted from a laser diode that can be used in the fluorescence spectrometer illustrated in FIG. 1.
Figure 3B:
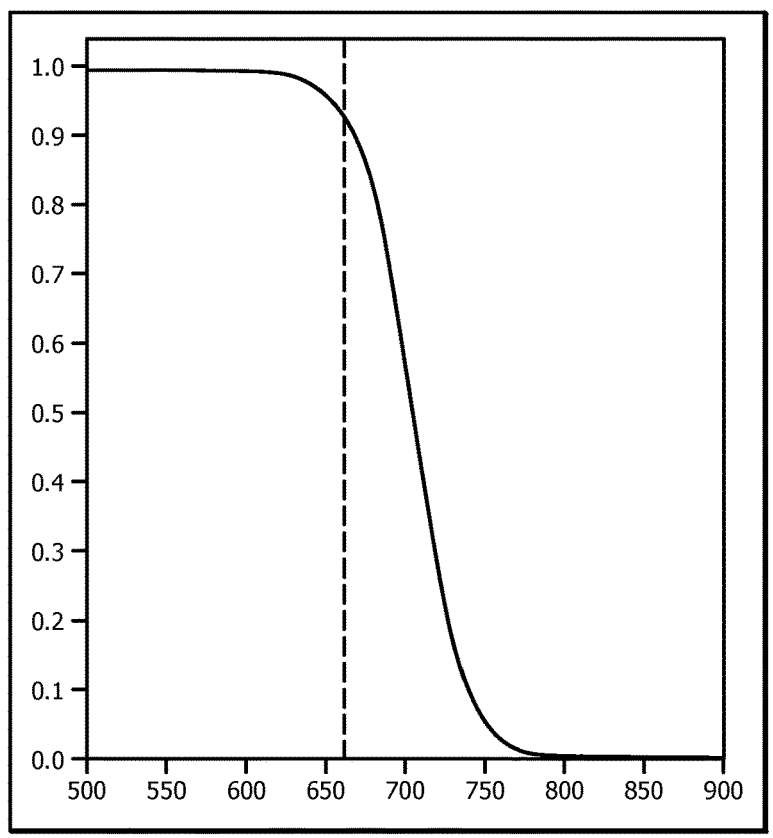
FIG. 3B illustrates an example of the active target spectrum range of a short-pass optical filter that can be used in the fluorescence spectrometer illustrated in FIG. 1.

FIG. 2 illustrates a diagram of optical elements that can be used in the fluorescence spectrometer illustrated in FIG. 1. A sample 102 in vial 120 is irradiated with light emitted from a light source, e.g., either a laser or light-emitting diode 101. FIG. 3A illustrates an example of a spectrum of light that can be emitted from laser 101. Specifically, the light emitted by the light source may be focused by a lens 207 and passed through a short-pass optical filter 201 optimized for the light source. The optical filter 201 is utilized and designed to prevent longer wavelengths of light from the illumination source that would interfere with the emission signal 205 of the sample 102 being cast onto the detector 103. FIG. 3B illustrates an example of an active target spectrum range of the short-pass optical filter 201 and the attenuation of the longer wavelengths.

Figure 3C:
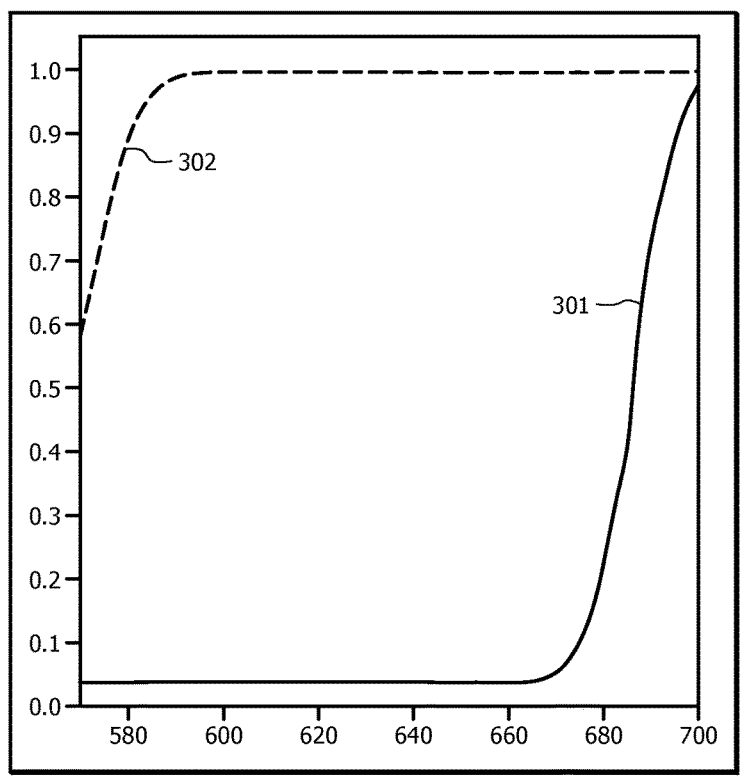
FIG. 3C illustrates an example of the "s" and "p" polarizing states of a polarizing cubic beam splitter element that can be used in the fluorescence spectrometer illustrated in FIG. 1.
Figure 3D:
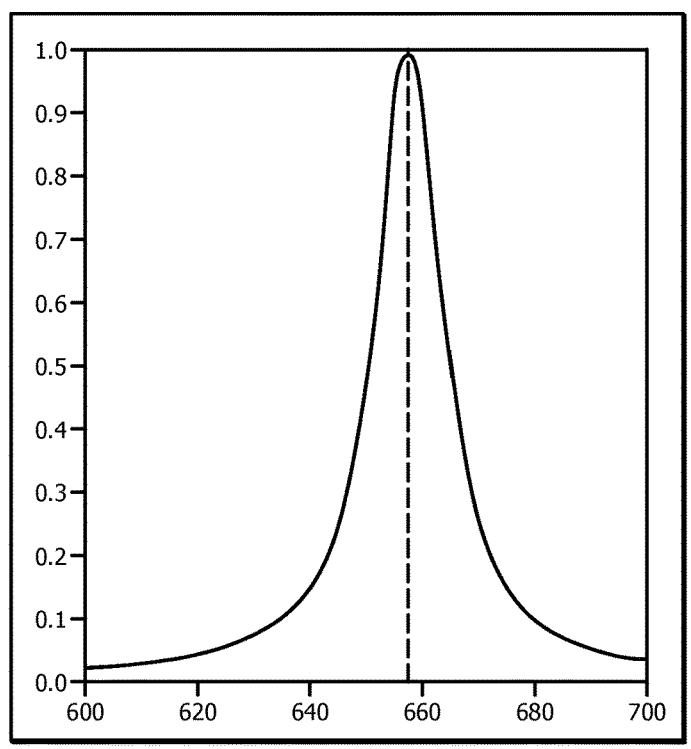
FIG. 3D illustrates an example of a spectrum of excitation light that could be produced to illuminate a sample using the fluorescence spectrometer illustrated in FIG. 1.

After passing through the short-pass filter 201, the light from the excitation source may be cast upon a polarizing cubic beam splitter element 202. Light from the source 101 in the "s" polarization state (the excitation light 204) is reflected towards and focused onto the sample 102 in vial 120. Light in the "p" polarization state (light 208) passes through the cube 202 and out of the path of the optical system. FIG. 3C illustrates an example of the "s" and "p" polarizing states of the polarizing cubic beam splitter element that 202 (curves 301 and 302, respectively). In the case of a laser diode, all of the light output is natively polarized, and during construction of the optical system alignment, the diode allows for nearly all of the desired wavelengths of light generated by the source 101 to be focused onto the sample 102. FIG. 3D illustrates an example of a spectrum of excitation light 204 that could result after passing through cube 202, which excitation light 204 is then used to illuminate sample 102.

Figure 3E:
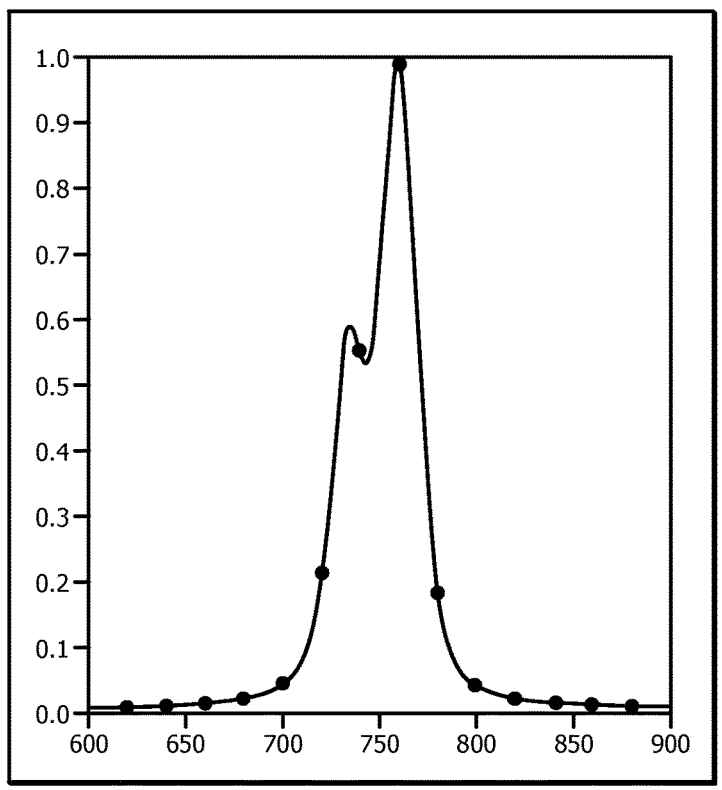
FIG. 3E illustrates an example of a spectrum of emission light that could be generated by an illuminated sample that can be used in the fluorescence spectrometer illustrated in FIG. 1.

Upon illumination of the sample 102 using excitation light 204, emission light 205 from the taggant (as well as fluorescence emission from the sample, e.g., from a fuel matrix) is generated. FIG. 3E illustrates an example of a spectrum of emission light 205 that could be generated by the illumination of sample 102. In any event, the light source is operable for providing excitation light on the liquid sample 102 in the liquid sample container 120.

Figure 3F:
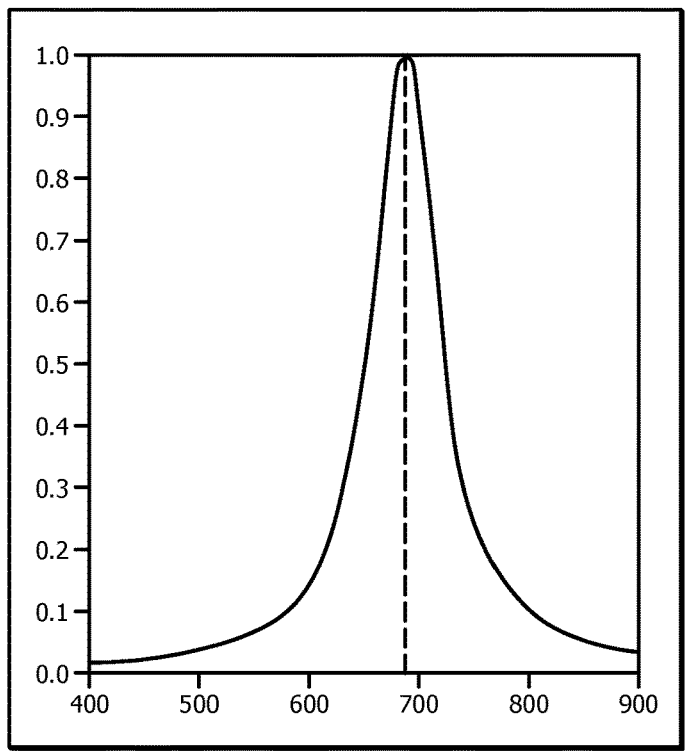
FIG. 3F illustrates an example of an active target spectrum range of a long-pass optical filter that can be used in the fluorescence spectrometer illustrated in FIG. 1.

The emissive light 205 is collected back into the optical system by the collection optics passed through the polarizing beam splitter cube 202 allowing emission light of the "p" polarization state to pass (emission light 209). The emission light 209 may then pass through a long-pass optical filter 203, which further reduces any refracted/scattered light from the excitation source 101 from entering the optical detector 103. FIG. 3F illustrates an example of an active target spectrum range of the long-pass optical filter 203 and the attenuation of the shorter wavelengths.

Figure 3G:
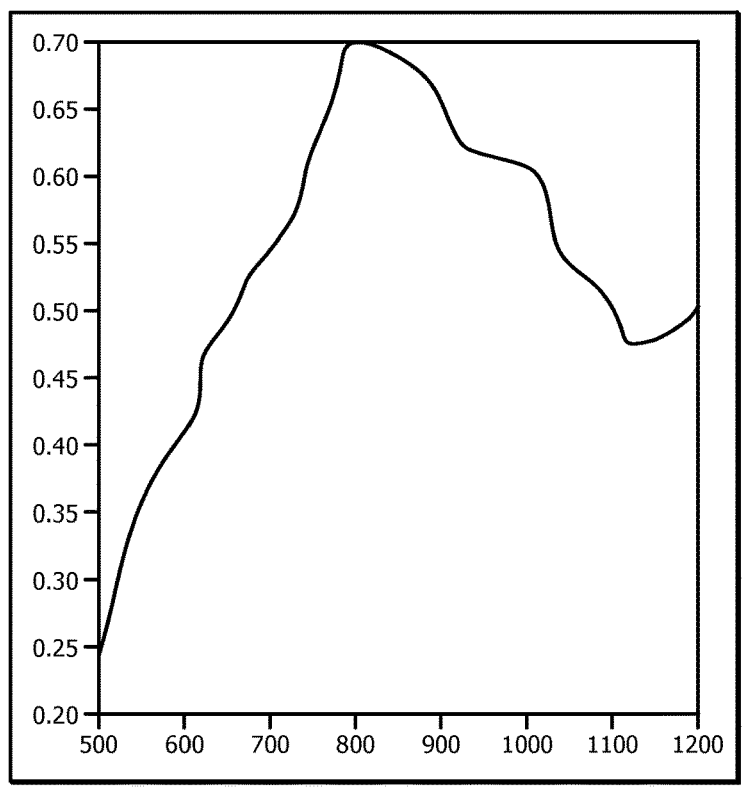
FIG. 3G illustrates grating efficiency of an example of a diffraction grating that can be used in the fluorescence spectrometer illustrated in FIG. 1.

After passing through the long-pass optical filter 203, emission light 209 from the sample 102 may then enter the optical detector 103 through a fixed slit 210, which acts as an entrance aperture. The light may then reflect off of a collimating mirror 206 onto a diffraction grating 211 separating the light into its spectral components based on the groove density and blaze wavelength of the selected grating. FIG. 3G illustrates an example of the grating efficiency of diffraction grating 211. In any event, the optical detector 103 is operable for measuring the emission spectra emitted from the liquid sample 102.

Figure 3H:
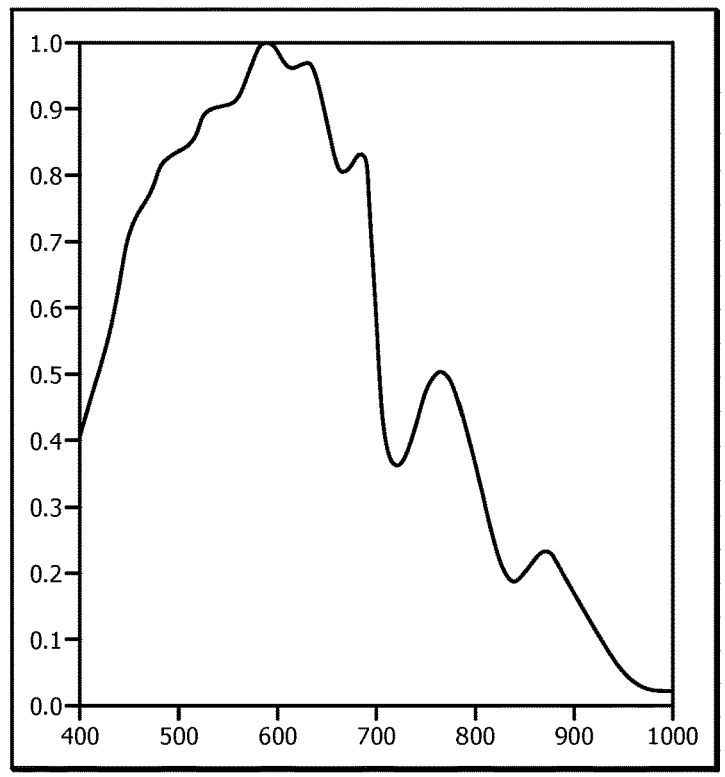
FIG. 3H illustrates an example of a spectrum of light that would be detected by the detector elements that can be used in the fluorescence spectrometer illustrated in FIG. 1.

Separated light from the diffraction grating 211 may then be cast upon a focusing mirror 212, which reflects the light onto the detector elements 213 (e.g., a 2048 element linear CCD array). FIG. 3H illustrates an example of a spectrum of light that could be detected by the detector elements 213. The detector elements 213 convert the photons of light hitting the individual CCD elements into an electrical signal, which is captured on an electrical board in the spectrometer 103 where it may be transferred, e.g., via a USB connection to a computer or other signal processing module 105 for data processing and display 108 (such as a touch screen panel PC). In any event, a signal processing module 105 is operably connected to the optical detector 103 to obtain the measured emission spectra of the liquid sample 102 from the optical detector 103. The computer 105 may include a memory unit operable for storing a computer program for operating the portable device 100, and a processor coupled to the memory unit, wherein the processor is operable for operating the portable device 100 in response to the computer program. In embodiments of the present invention, the computer 105 has a microcontroller 112 and laser drive 113. Microcontroller 112 may include a processor core, memory, and programmable input/output peripherals.

An alternate optical arrangement may be employed in which the polarizing cubic beam splitter 202 is not utilized. A laser or light emitting diode may be arranged in a perpendicular plane to the above-described detector. An alternate set of collection optics may then be employed to efficiently collect the emission light 205 from the sample 102 and transfer said light 205 onto the detector 103. In this embodiment, the previously described long-pass and short-pass optical filters may still be utilized in the described fashion.

Power may be supplied to the system through the power supply board 106. The supply board 106 may be connected to a battery or batteries 109 (such as a rechargeable battery), which provide power to the unit when it is not plugged into an AC outlet. The power supply board can be connectable to a power supply 114 (such as a DC power supply). The power supply board 106 may contain charging circuits for the battery or batteries 109 (such as a battery monitor 115 and battery charger 116). The power supply board 106 additionally may contain individual power circuits that supply the appropriate voltage and current for the controller board 105, temperature regulator 104 and temperature regulator controller 110, and panel PC 108 (interface module power supply 117, temperature regulator power supply 118, and panel PC power supply 119, respectively). The temperature regulator may be a TEC.

The temperature regulator (e.g., TEC) 104, in an embodiment, is a Peltier device, which transfers heat from one side of the device to the other side against the temperature gradient based on the application of a DC voltage. In application here, the optional temperature regulator or Peltier device is used to regulate the temperature of the illumination light source 101, optical detector 103, and sample 102, or of any one or two of them. Temperature regulation of these components affords several advantages. First, it extends the external operating temperature range of the platform, in particular, as the TEC 104 may be controlled by a dual stage regulator. The TEC or other temperature regulator is in this embodiment capable of heating the optical system when the ambient temperature is low and cooling the optical system when the ambient temperature is elevated. Ensuring a constant temperature further alleviates changes in the fluorescence intensity of the chemical compound based on temperature of the sample. This also affords advantages by stabilizing the response from the CCD-based detector allowing for more accurate fluorescent readings across the range of operating temperatures.

The TEC 104 may be mounted to a support, e.g., an aluminum plate, in which are all of the optical components including, the illumination source 101, optical detector 103, and sample vial 120. The aforementioned components may be affixed to the TEC 104 such that intimate thermal contact between the components is achieved. The TEC controller 110 may regulate the temperature of the optical system based on a thermal couple affixed to or located inside the optical detector 103 by a feedback loop system. When the temperature of the optical system, e.g., reported by the thermal couple, is determined to be outside of a specified range, the TEC controller 110 (or other temperature regulator controller) regulates the TEC 104 (or other temperature regulator) to either heat or cool the optical system until the specified range is achieved.

Optionally, a thermal gap pad 111 can be positioned between the TEC 104 and the optical detector 103.

The optical detector 103 may transfer acquired spectra to a signal processing module, e.g., microprocessor unit 105, on which the data analysis is performed. The microprocessor unit 105 in one embodiment may be an embedded panel PC, laptop computer, PDA, or cell phone, including an integrated mainboard equipped with a CPU, touch screen LCD interface, and protective housing with industry standard input/output connectors including USB, RS-232, 10/100 Mbps ethernet, and data storage in the form of compact flash card socket.

The plurality of output options typically associated with the microprocessor unit enable a variety of reporting features for the device. Upon testing, data or results from analyses stored locally on the device may be transmitted to a web enabled database, emailed, or otherwise distributed for near real-time viewing by others.

Once the spectral data has been collected and transferred to the microprocessor unit 105, the data can be utilized to extract out the information of the quantity of fluorophore present, if any, in the tested sample, using one or more of the methods discussed and described herein.

An additional feature disclosed herein is an ability of a spectral library to be loaded and transferred from instrument to instrument without the need to analyze dozens of standards on each device. This is advantageous for instrumentation that is deployed in the field where laboratories are not accessible for the production of dozens of calibration standards for potentially a multitude of markers. To overcome this challenge, a system for normalizing the spectrometer response and intensity of the excitation source can be utilized.

For normalizing the spectral response of detectors across multiple units, a broad-based fluorescence sample, which provides a signal across the entire region of interest, may be acquired on a lab-based fluorescence spectrometer (or designated portable instrument utilized as a "gold standard"). As used herein, the term "gold standard" or "gold instrument" refers to a device of the present invention that is kept in a controlled lab environment and serves as the reference device from which the calibration of all future devices produced are derived. The spectrum data array obtained from the specified "gold instrument" may be then divided by the spectral array from the instrument being calibrated. The resultant matrix, noted by the instruments transfer function, may be stored in a memory device. Subsequent sample data obtained on the instrument may be then multiplied by the units transfer function yielding spectral data consistent with the "gold instrument."

Figure 4:
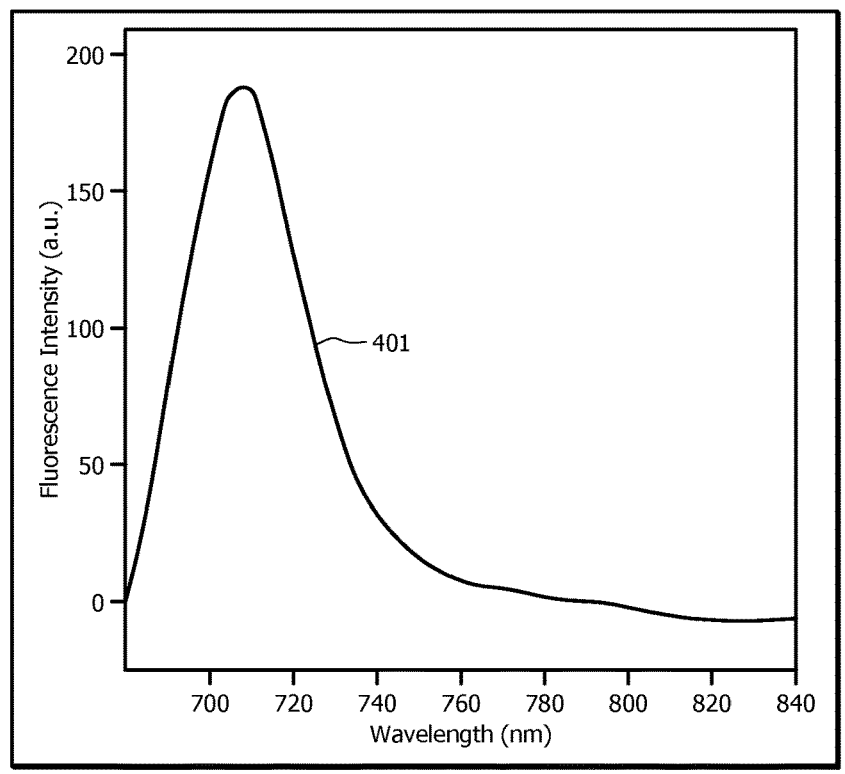
FIG. 4 illustrates an example of a spectrum of a fluorescent taggant in a clean solvent.

A second step of the standardization is that of the illumination source. For normalizing illumination sources, a standard of taggant may be measured in the instrument in a clean solvent on both the lab-based "gold instrument" and the unit being calibrated. FIG. 4 illustrates an example of a spectrum 401 of a fluorescent taggant in a clean solvent. The ratio of the intensity of the standard taggant sample in the "gold instrument" to the instrument being calibrated is determined and may be stored in memory. Subsequent sample data obtained on the instrument may be then multiplied by the unit's intensity multiplier yielding spectral data consistent with the "gold instrument."

A process utilized in some implementations of the present invention involves spectral preprocessing, i.e., optimizing the signal intensity of the sample. Initially, a spectrum of the sample is obtained and its peak intensity determined. If the intensity is outside of a desired range, the integration time of the detector may be adjusted to bring the signal intensity into the desired range. Once an optimal integration time has been established, a series of spectra may be recorded and averaged at that set time for the purposes of signal noise reduction. Once the averaged spectrum has been obtained, the intensity at each spectral wavelength may be divided by the integration time producing a spectrum whose intensity may be directly compared to other spectra obtained at different integration time.

As a result of the high resolution full spectral data afforded by embodiments of the present invention, the spectral data collected may be processed ("data analysis") by several different methods, all of which afford advantages over systems currently described in the patent literature, or currently in use in the field.

The taggant (or taggants) may be selected to have an emission fluorescence somewhere in a range of from about 500 nm to about 900 nm. Moreover, when more than one taggant is used, the taggants have emission fluorescence that are different from one another (i.e., the second taggant has a different emission fluorescence spectrum than the first taggant, and the third taggant has a different emission fluorescence spectrum than the first and second taggants, and so on). Moreover, these different emissions from the taggants are generated from the same light source.

Background Subtraction Analysis.

Native fluorescence background subtraction and integration. One such approach involves the fitting and subsequently subtracting the background fluorescence of the sample associated with the background of the fuel or other liquid, leaving only the fluorescence signal associated with the fluorescent taggant. In the embodiments of the present invention, it has been found that the background fluorescence exhibited by fuels can be well fit by a variety of common mathematical expressions. For example, a quadratic equation, an exponential equation, a linear combination of two exponential curves or higher order polynomial equations provide an excellent fit for the observed fluorescence background of the fuel. For this process, data points at wavelengths prior to that of the taggant emission and after the taggant emission are selected and the selected mathematical expression is optimized via an established nonlinear optimization technique. The calculated background spectrum is then subtracted from the original data spectrum. The result of the spectral subtraction is a spectrum in which the signal present is associated with only that of the fluorescent taggant. At this point, quantification of the taggant by conventional techniques such as spectral integration or peak height analysis is highly accurate as a result of the prior background fluorescence subtraction.

This method of analysis is advantageous for the analysis of taggants whose spectral response is relatively insensitive to solvatochromic effects yet allows for the analysis of these taggants in fuels of widely variable fluorescence backgrounds.

Example No. 1 Detection Of Kerosene In Diesel Fuel.

Governments of countries often subsidize a fuel product such as kerosene to provide a low cost fuel for economically depressed households for a source of energy for cooking and lighting. However, these programs are often subject to widespread abuse. Subsidized kerosene is sold at much lower prices than gasoline or diesel and is frequently diverted by corrupt groups for use as a transport fuel.

Figure 5A:
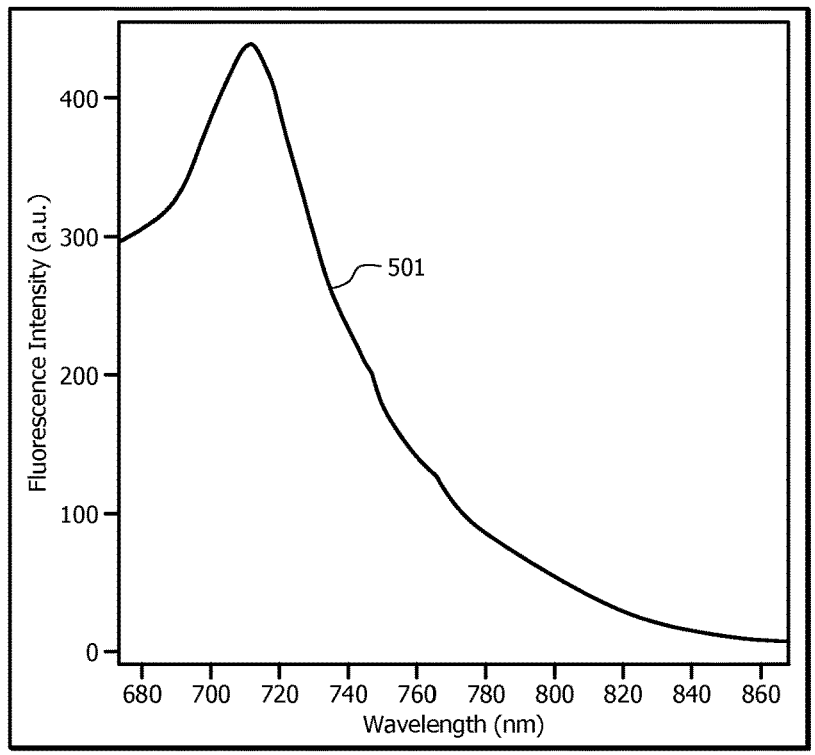
FIG. 5A illustrates an example of a spectrum of a fluorescent taggant in a fuel possessing background fluorescence.

For this example, a kerosene sample was dosed at 200 parts per billion (ppb) (w/w) with a fluorescent taggant (e.g., NIR Fluorophore: $BF_2$ Chelated [3,5-di-(4-methoxyphenyl)-5-phenyl-1H-pyrrol-2-yl)]-[3-(4-methoxyphenyl)-5-phenylpyrrol-2-ylidene]amine). The marked kerosene was then added into samples of five different diesel fuels of varying origin. The diluted diesel sample was then analyzed by two different methods, first with an instrument disclosed in U.S. Pat. No. 5,525,516 (a filtered photodiode-based fluorescence detector), which is hereby incorporated by reference herein, and second the device and analysis method #1 described above. For both devices, a 658 nm laser diode was used as an excitation source for the sample. Both devices were calibrated on a standard of the fluorescent taggant in a diesel fuel at a concentration of 100 ppb (w/w). FIG. 5A illustrates the spectrum 501 that was measured for one of the five diesel fuels being sampled. Spectrum 501 includes both the spectrum due to the fluorescent taggant and the background fluorescent due to the diesel fuel.

The background fluorescence (resulting from the diesel fuel) was calculated and subtracted from the acquired spectrum. The background fluorescence was fit by a quadratic function, generalized in equation (1).

$$f(x)=ax^2+bx+c, \text{ where } a \neq 0 \qquad (1)$$

Three points selected for fitting in this example were 687 nm, 820 nm, and 879 nm. For this method, the three points were selected at wavelengths where the taggant did not provide significant fluorescence emissions (i.e., all or nearly all of the fluorescence emissions were due to the fuel, not the taggant). The points were further selected to be separate and distinct from one another, including that (a) at least one of the points (in this case at a wavelength of 687 nm) was selected at a wavelength that was shorter than the range of wavelengths where the taggant was known to have significant fluorescence emissions and (b) at least one of the points (in this case at a wavelengths of 820 nm and at a wavelength of 879 nm) was selected at a wavelength that was longer than the range of wavelengths where the taggant was known to have significant fluorescence emissions.

Figure 5B:
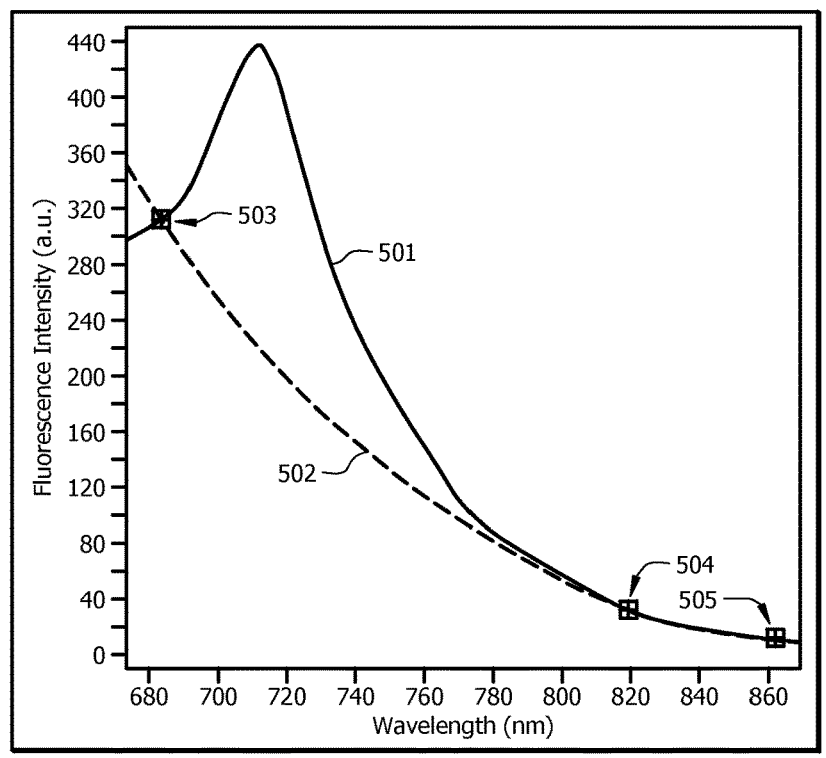
FIG. 5B illustrates an example of the spectrum of the fluorescent taggant in fuel shown in FIG. 5A with a modeled fluorescent background overlaid.

From the initial parameters a=0.00001, b=−1.0, and c=660, a Nelder-Mead optimization (downhill simplex) was performed, minimizing the squared difference of the calculated quadratic from the sample spectrum at the aforementioned wavelengths. Once the squared difference was below an accepted tolerance (in this case, tolerance=1.0×10−12) or a maximum number of iterations (in this case, 15,000) were completed, the calculated background spectrum ($Q_{calc}$) was established. FIG. 5B illustrates the spectrum 501 (which is the same as the spectrum 501 illustrated in FIG. 5A) with the calculated background spectrum ($Q_{calc}$) 502 overlaid. Points 503, 504, and 505 correspond to the three points selected for fitting the calculated background spectrum (were 687 nm, 820 nm, and 879 nm, respectively). As is reflected in FIG. 5B, the spectrum (such as spectrum 501) and the calculated background spectrum (such as calculated background spectrum 502) generally will intersect at the three points selected for modeling the background spectrum.

The calculated background spectrum ($Q_{calc}$) is subtracted from the sample spectrum ($Q_{sample}$), which generates a background subtracted spectrum (QBG sub) (see equation (2)), which was passed into the marker quantification routine.

$$Q_{BG\ sub}=Q_{sample}-Q_{calc} \qquad (2)$$

Figure 5C:
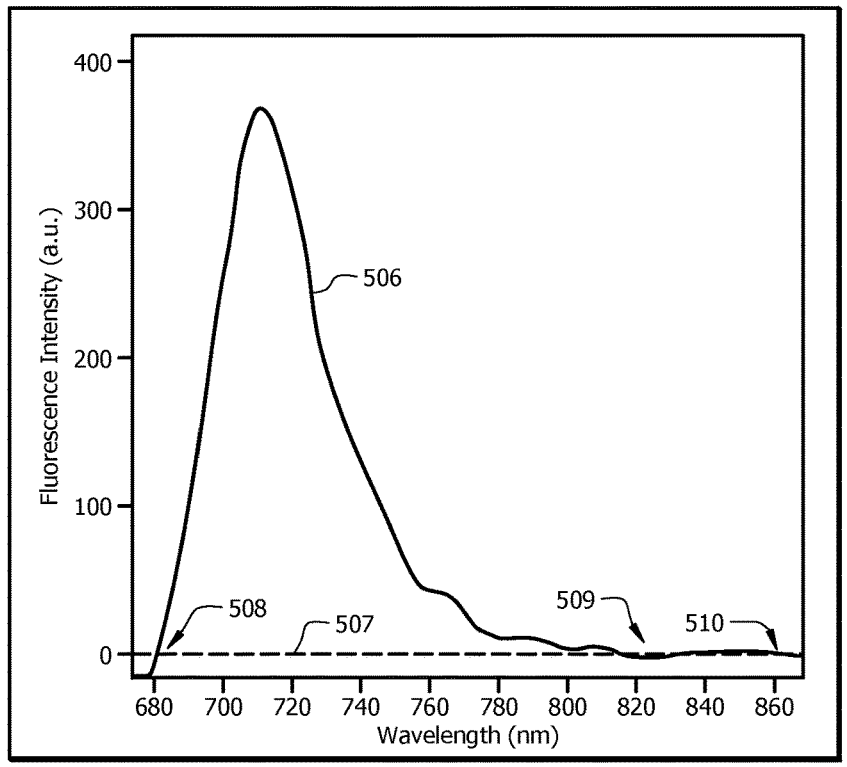
FIG. 5C illustrates an example of the spectrum of a fluorescent taggant in fuel after the modeled background fluorescence was subtracted.

FIG. 5C illustrates a background subtracted spectrum 506, which is spectrum 501 after the calculated background spectrum 502 was subtracted. Zero line 507 is shown, which represents zero fluorescence intensity. Points 508, 509, and 510 correspond to wavelengths 687 nm, 820 nm, and 879 nm, respectively. Because spectrum 501 and the calculated background spectrum crossed at these wavelengths (see points 503, 504, and 505 of FIG. 5B), background subtracted spectrum 506 has zero fluorescence intensity at each of points 508, 509, and 510.

For quantification, the intensity values over the region of interest (ROI=687-840 nm) were summed by equation (3):

$$\Sigma_{687\,nm}^{840\,nm} Q_{BG\,sub} \quad (3)$$

The sum of the intensities calculated for the sample was divided by the sum of the intensities for the standard sample, which in turn was multiplied by the concentration of the standard giving the concentration of the unknown.

The results of the analysis by these two methods (the filtered photodiode-based fluorescence detector and the device and background subtraction analysis method described above) are reflected in Table 1 and Table 2, respectively. As used herein, to "predict" the taggant concentration means to analyze the data measured from a sample (such as by performing a background subtraction analysis method and/or a multivariate analysis method of the sample) to yield a determination of the concentration of the taggant in the sample (the "predicted concentration" of the taggant in the sample).

TABLE 1

Filtered Photodiode Detector

| Fuel Sample No. | Act. Taggant Conc. (ppb) | Predicted Conc. (ppb) | Conc. Difference from Actual (ppb) | % Difference from Actual |
|---|---|---|---|---|
| Diesel-1 | 25 | 20.2 | −4.8 | −19.2% |
| Diesel-2 | 25 | 18.9 | −6.1 | −24.4% |
| Diesel-3 | 20 | 29.1 | 9.1 | 45.5% |
| Diesel-4 | 20 | 23.6 | 3.6 | 18.0% |
| Diesel-5 | 20 | 16.0 | 4.0 | −20.0% |
| Standard Deviation of Diff from Actual | | | 6.5 ppb | 30.7% |

TABLE 2

Present Device (Background Subtraction Analysis Method)

| Fuel Sample No. | Act. Taggant Conc. (ppb) | Predicted Conc. (ppb) | Conc. Difference from Actual (ppb) | % Difference from Actual |
|---|---|---|---|---|
| Diesel-1 | 25 | 25.8 | 0.8 | 3.2% |
| Diesei-2 | 25 | 23.1 | −1.9 | −7.6% |
| Diesel-3 | 20 | 19.0 | −1.0 | −5.0% |
| Diesel-4 | 20 | 19.1 | −0.9 | −4.5% |
| Diesel-5 | 20 | 20.8 | 0.8 | 4.0% |
| Standard Deviation of Diff from Actual | | | 1.2 ppb | 5.2% |

The results in Table 1 and Table 2 show a greatly increased accuracy in detection of the fluorescent taggant using the present device (background subtraction analysis method) described above over that of a simple photodiode based fluorometer of the prior art.

Such results show that the background subtraction analysis method is able to determine the concentration of the sample, e.g., sample fuel, within 10% of the actual taggant concentration of that sample, e.g., sample fuel, and typically is able to do so within 5% of the actual taggant concentration of the sample, e.g., sample fuel. When, the concentration of the taggant in the sample or fuel is relatively low (i.e., less than about 1000 ppb, and more typically less than about 100 ppb), it is important to obtain measurements within a tight tolerance (i.e., a standard deviation of less than 10% and, more typically, a standard deviation of less than 5%). For instance, as shown in Table 2, a 1.2 ppb difference in measuring of the taggant concentration results in a difference in the predicted concentration and actual concentration of about 5.2%. In some embodiments of the present invention, the concentration of the taggant in the fuel is in the range from about 10 ppb to about 50 ppb.

Multivariate Analysis.

Another data analysis approach is to employ a multivariate analysis for the quantification of a taggant in a variable fuel matrix.

For this method, a spectral training set, which includes the taggant of interest at various concentrations in a variety of liquid matrices, is produced. The breadth of the training set may capture the full variety of solvent environments that would likely be encountered by the taggant in the field. This includes a variety of aromatic and aliphatic solvents, a range of available fuels with variable background fluorescence, a range of fuels with variable concentrations of oxygenates and bio-derived components. The training set may also contain the taggant in a variety of industrial solvents commonly used to adulterate fuel. The training set may also include the spectra of common fuel dyes, additives, or chemical compounds commonly found in the fuels and potentially could be found in the unknown testing matrix.

The spectral data from the training set then undergoes a multivariate regression analysis. Partial least squares (PLS) analysis, principal components regression (PCR) analysis, and many other related multivariate analyses may be used singularly or in combination for this analysis. The output of this analysis is a calibration model consisting of an array of regression parameters or coefficients (one for each wavelength channel), that represents a pattern in n-dimensions (where n is the number of wavelength channels) that is uniquely correlated to the taggant and uncorrelated to other spectral interferences. This calibration model is then applied to the spectrum of an unknown sample to predict the taggant concentration in the unknown samples.

This method of analysis is advantageous for taggants which undergo notable solvatochromic shifting.

Example No. 2 Dilution Of Premium Branded Gasoline.

For petroleum companies who develop proprietary fuel additive packages, it is important to verify that the fuel additive is present and at the appropriate concentration in the finished gasoline to provide the level of performance promised to a customer. It is not uncommon for independent corrupt station owners to dilute premium branded fuel products with either market generic fuels or other inexpensive industrial solvents. This practice is financially advantageous since market generic fuels and solvents are often cheaper than branded premium fuels.

For this example, a premium branded gasoline sample was dosed at 30 ppb (w/w) with a florescent taggant (e.g., NIR Fluorophore: 1[4], 8[11], 15[18], 22[25] Tetrakis [[4-[2-ethylhexyloxy]carbonyl]phenoxy]phthalocyanine). The marked gasoline was then diluted with samples of five different fuels of varying origin. The diluted gasoline samples were then analyzed by two different methods, first an instrument disclosed in U.S. Pat. No. 5,525,516 (a filtered photodiode-based fluorescence detector) and secondly the device and analysis method #2 described above. For both devices, a 658 nm laser diode was used as an excitation source for the sample. The filtered photodiode-based device was calibrated on a solution of the fluorescent taggant in gasoline at a concentration of 100 ppb (w/w). A calibration model was generated from a training set of 10 fuels of varying origin, using a 7 factor partial least squares regression analysis in accordance with the disclosed method.

For data analysis, a partial least squares (PLS) regression was performed on a training set of samples of known taggant concentration. For this example, the training set was composed of 10 gasoline samples acquired from various gas stations throughout a region, which were marked with the fluorescent taggant at the following concentrations (0, 5, 25, 100 ppb (w/w)). The aforementioned spectra (600-1000 nm) of the samples from the training set (X) were regressed against the corresponding marker concentrations (y). The inverse of an n×m calibration matrix of spectra (where n samples over m wavelengths) is estimated as follows (equation (4)):

$$X^+ = W \times (P^T W)^{-1} \times (T^T T)^{-1} \times T^T \quad (4)$$

is the m×p loadings matrix, W is the m×p matrix of weights, T is the n×p matrix of scores, and p is the number of PLS latent variables. Latent variables are pseudo-variables that replace the original wavelength variables in the PLS model. Latent variables have the desired quality of being orthogonal to one another (i.e., not linearly correlated) and are thus easier to invert. The superscript T denotes matrix transposition. There are several closely linked PLS algorithms that those skilled in the art could used in estimating W, P, and T from the training spectra X and the concentration values y, which would render similar results. The elements of P are the weights all m wavelengths, T contains the original spectral data in a rotated coordinate system, and W are additional weights that ensure that the columns of T are orthogonal.

The regression vector (b) was estimated from the inverse matrix X+ and the calibration concentration vector y as in equation (5).

$$B = X^+ \times y \quad (5)$$

For prediction of unknowns, the regression vector calculated above in equation (5) was used to calculate the concentration of taggant in the unknown as follows in equation (6):

$$y_p = X_{pred} \times b^T \quad (6)$$

$X_{pred}$ is the matrix of the unknown sample. $y_p$ is the vector of estimated concentration.

The results of the analysis by these two methods (the filtered photodiode-based fluorescence detector and the device and multivariate analysis method described above) are reflected in Table 3 and Table 4, respectively.

TABLE 3

| | Filtered Photodiode Detector | | | |
|---|---|---|---|---|
| Fuel Sample No. | Act. Taggant Conc. (ppb) | Predicted Conc. (ppb) | Conc. Difference from Actual (ppb) | % Difference from Actual |
| Gasoline-1 | 25 | 20.6 | −4.4 | −17.6% |
| Gasoline-2 | 25 | 19.9 | −5.1 | −20.4% |
| Gasoline-3 | 25 | 35.0 | 10.0 | 40.0% |
| Gasoline-4 | 20 | 21.9 | −3.1 | −12.4% |
| Gasoline-5 | 20 | 23.2 | 3.2 | 16.0% |
| Standard Deviation of Diff from Actual | | | 6.4 ppb | 26.1% |

TABLE 4

| | Present Device (Multivariate Analysis Method) | | | |
|---|---|---|---|---|
| Fuel Sample No. | Act. Taggant Conc. (ppb) | Predicted Conc. (ppb) | Conc. Difference from Actual (ppb) | % Difference from Actual |
| Gasoline-1 | 25 | 26.1 | 1.1 | 4.4% |
| Gasoline-2 | 25 | 25.2 | 0.2 | 0.8% |
| Gasoline-3 | 20 | 24.2 | −0.8 | −3.2% |
| Gasoline-4 | 20 | 23.9 | −1.1 | −4.4% |
| Gasoline-5 | 20 | 19.2 | −0.8 | −4.0% |
| Standard Deviation of Diff from Actual | | | 0.9 ppb | 3.8% |

The results in Table 3 and Table 4 show a greatly increased accuracy in detection of the fluorescent taggant using the present device (multivariate analysis method) described above over that of a simple photodiode based fluorometer of the prior art.

Similar as for the background subtraction analysis method, such result show that the multivariate analysis method is able to determine the concentration of the sample fuel within 5% of the actual taggant concentration of the sample fuel. Again, given the relatively low concentrations being predicted here, such accuracy in results in the ability to measure the concentration of the taggant in the fuel within a standard deviation accuracy of less than 1 ppb (and a difference of less than 5%.)

Example No. 3 Multiple Marker Detection.

It is often the case that several brand owners within the same geographic region will want to utilize the same or similar marking technologies. It is anticipated that this will continue to be the case for the present invention. For such circumstance, a brand owner will sometimes use two or more fluorescent taggants (with each fluorescent taggant at its own predetermined concentration) as this will render it unlikely that another brand owner in the same geographical region would use the same combination of taggants (and particularly at such predetermined concentrations).

However, it is highly likely that the two (or more) fluorescent taggants used will exhibit a degree of spectral overlap because (a) the fluorescence of organic fluorophores encompasses a relatively wide wavelength range (i.e., a width of 50-150 nm) and (b) the practical marking range within the NIR region is relatively small (i.e., wavelength range of 600-1000 nm).

Conventional instrumentation does not provide a mechanism whereby the signals from the two (or more) taggants can be differentiated. However, as a result of the ability of the present invention to analyze the full fluorescence spectrum, the present invention can accurately quantify a particular fluorescent taggant of interest in the presence of a one or more other fluorescent taggants, and can additionally quantify the concentrations of the two (or more) taggants present in the analyzed sample.

Thus, the present invention provides incredibly insight and valuable information regarding the tested sample. For instance, when a sample is diluted, the present invention has the capacity provides a tool to for identifying and quantifying the second fuel or industrial solvent that was used to dilute the sample.

For this example, branded diesel fuels were dosed at 50 ppb (w/w) with the fluorescent taggant (Taggant #1), $BF_2$ Chelated [3,5-di-(4-methoxyphenyl)-5-phenyl-1H-pyrrol-2-yl)]-[3-(4-methoxyphenyl)-5-phenylpyrrol-2-ylidene] amine), and a sample of kerosene was dosed at 50 ppb (w/w) with the fluorescent taggant (Taggant #2), 16,17-Bis(octyloxy)anthra[9,1,2-cde-]benzo[rst]pentaphene-5,10-dione representing a subsidized fuel from the region or another branded product within the same geographic region. Samples of the fuels were then mixed and analyzed by two different methods, first an instrument disclosed in U.S. Pat. No. 5,525,516 and the multivariate analysis technique described by the present invention. For both devices, a 658 nm laser diode was used as the excitation source for the samples. The instrument of U.S. Pat. No. 5,525,516 was calibrated using a sample of diesel fuel marked at 50 ppb (w/w) with $BF_2$ Chelated [3,5-di-(4-methoxyphenyl)-5-phenyl-1H-pyrrol-2-yl)]-[3-(4-methoxyphenyl)-5-phenylpyrrol-2-ylidene]amine).

A calibration model for the instrument of the present invention was generated from a training set of 15 fuels of varying origin at various marking levels, using a 7 factor PLS2 regression analysis in accordance with the disclosed teachings. Mathematically, the PLS2 regression analysis is essentially analogous to the PLS1 analysis demonstrated in Example No. 2, only for PLS2 regression analysis the concentrations of both taggants are input into the model. When analyzing unknown samples, the PLS2 regression analysis allows for the quantification of both markers in an unknown sample simultaneously and for these examples provided a negligible difference in the accuracy and precision of the taggant level determination, as compared to the PLS1 model of Example No. 2.

When building the model the concentrations of both markers in the samples are input for each member of the training set. Upon regression analysis, the resulting calibration model contains spectral features associated with each marker, thus allowing both marker levels to be determined simultaneously in unknown samples. This approach has the additional advantage of capturing changes in the spectral features of the markers in the event that they interact with one another.

The samples for the training set in the current example include a set 15 diesel fuels tagged at various concentrations (0, 5, 25, and 50 ppb) of combinations of the aforementioned taggants. For example, the current training set included samples of diesel fuel marked at 50 ppb of both taggants #1 and #2, 50 ppb of taggant #1 and 25 ppb of taggant #2, etc.

The results presented in Table 5 and Table 6 demonstrate the utility of the PLS2 analysis in the simultaneous determination of both fluorescent taggants in the fuel samples over the samples analyzed by the filtered photodiode-based detector. It is also worth reiteration that because of the limitation of the filtered photodiode-based detector it does not possess the ability to differentiate between signals from the two marker structures, and as such the quantification is rather inaccurate.

Moreover, the library can also be focused such that certain variables are eliminated, which again increases the accuracy of the device and method of the present invention.

TABLE 5

| | Filtered Photodiode Detector | | | |
|---|---|---|---|---|
| Fuel Sample No. | Act. Taggant Conc. (ppb) | Predicted Conc. (ppb) | Conc. Difference from Actual (ppb) | % Difference from Actual |
| Taggant No. 1 | | | | |
| Diesel 1 | 20 | 32.1 | 12.1 | 60.5% |
| Diesel 2 | 20 | 32.7 | 12.7 | 63.5% |

TABLE 5-continued

| | Filtered Photodiode Detector | | | |
|---|---|---|---|---|
| Fuel Sample No. | Act. Taggant Conc. (ppb) | Predicted Conc. (ppb) | Conc. Difference from Actual (ppb) | % Difference from Actual |
| Diesel 3 | 20 | 31.3 | 11.3 | 56.5% |
| Diesel 4 | 10 | 15.6 | 5.6 | 56.0% |
| Diesel 5 | 20 | 26.9 | 6.9 | 34.5% |
| Diesel 6 | 10 | 20.0 | 10.0 | 100.0% |
| Diesel 7 | 50 | 48.0 | −2.0 | −4.0% |
| Standard Deviation of Diff from Actual | | | 5.2 ppb | 31.6% |
| Taggant No. 2 | | | | |
| Diesel 1 | 20 | n/a | n/a | n/a |
| Diesel 2 | 20 | n/a | n/a | n/a |
| Diesel 3 | 20 | n/a | n/a | n/a |
| Diesel 4 | 10 | n/a | n/a | n/a |
| Diesel 5 | 10 | n/a | n/a | n/a |
| Diesel 6 | 20 | n/a | n/a | n/a |
| Diesel 7 | 0 | n/a | n/a | n/a |
| Standard Deviation of Diff from Actual | | | n/a | n/a |

TABLE 6

| | Present Device (Multivariate Analysis Method) | | | |
|---|---|---|---|---|
| Fuel Sample No. | Act. Taggant Conc. (ppb) | Predicted Conc. (ppb) | Conc. Difference from Actual (ppb) | % Difference from Actual |
| Taggant No. 1 | | | | |
| Diesel 1 | 20 | 20.8 | 0.8 | 4.0% |
| Diesel 2 | 20 | 19.2 | −0.8 | −4.0% |
| Diesel 3 | 20 | 20.5 | 0.5 | 2.5% |
| Diesel 4 | 10 | 10.4 | 0.4 | 4.0% |
| Diesel 5 | 20 | 21.4 | 1.4 | 7.0% |
| Diesel 6 | 10 | 10.8 | 0.8 | 8.0% |
| Diesel 7 | 50 | 48.7 | −1.3 | −2.6% |
| Standard Deviation of Diff from Actual | | | 0.96 ppb | 4.5% |
| Taggant No. 2 | | | | |
| Diesel 1 | 20 | 19.4 | −0.6 | −3.0% |
| Diesel 2 | 20 | 21.6 | 1.6 | 8.0% |
| Diesel 3 | 20 | 18.4 | −1.6 | −8.0% |
| Diesel 4 | 10 | 10.2 | 0.2 | 2.0% |
| Diesel 5 | 10 | 10.3 | 0.3 | 3.0% |
| Diesel 6 | 20 | 19.3 | −0.7 | −3.5% |
| Diesel 7 | 0 | 0.0 | 0.0 | 0.0% |
| Standard Deviation of Diff from Actual | | | 1.0 ppb | 5.2% |

For example, generally, the type of fuel (such as diesel) can be known or readily detected. Thus, a library could be restricted to only the data in the library utilizing that type of fuel. Also, for example, the geographic region of the fuel may be known. Thus, the library can be restricted to only the data in the library utilizing fuel from that geographic region By not including data points from the library that are not pertinent, the multivariate analysis method can be performed with increased accuracy.

Take for example that the library contained examples of a particular fluorescent taggant (NIR Fluorophore: $BF_2$ Chelated [3,5-di-(4-methoxyphenyl)-5-phenyl-1H-pyrrol-2-yl)]-[3-(4-methoxyphenyl)-5-phenylpyrrol-2-ylidene] amine) measured in all types of fuels from around the world. If the library was restricted to only those examples that contained diesel fuel from the Southern part of Italy, the multivariate analysis method of such a library will be more accurate in its predicted the taggant concentration of that taggant in such fuel.

Example No. 4 Dilution Detection.

The present invention can also be used to determine whether a fuel has been adulterated by dilution, even when the diluting agent is itself contains a different fluorescent taggant.

For example, a branded diesel fuel could be made by were dosing at 30 ppb (w/w) with the fluorescent taggant (Taggant #1), $BF_2$ Chelated [3,5-di-(4-methoxyphenyl)-5-phenyl-1H-pyrrol-2-yl)]-[3-(4-methoxyphenyl)-5-phenylpyrrol-2-ylidene]amine), and a sample of kerosene could be made dosed at 60 ppb (w/w) with the fluorescent taggant (Taggant #2), 16,17-Bis(octyloxy)anthra[9,1,2-cde-]benzo[rst]pentaphene-5,10-dione. As before the latter represents a subsidized fuel from the region or another branded product within the same geographic region.

The diesel fuel tagged with Taggant #1 can be diluted by adding the kerosene tagged with Taggant #2 at a 2:1 ratio (i.e., 66.7% diesel fuel and 33.3% kerosene), which is 50% dilution of the diesel fuel tagged with Taggant #1. Dilution factor is defined as shown in equation (7).

$$\text{Percent Dilution} = \frac{\text{Final Volume} - \text{Initial Volume}}{\text{Initial Volume}} \times 100\% \quad (7)$$

Due to the relationship among the final volume, the final taggant concentration, the initial volume, and the initial taggant concentration shown in equation (8), percent dilution can also be expressed as shown in equation (9).

$$\text{Final Volume} \times \text{Final } Conc = \text{Initial Volume} \times \text{Initial } Conc \quad (8)$$

$$\text{Percent Dilution} = \frac{\text{Initial } Conc - \text{Final } Conc}{\text{Final } Conc} \times 100\% \quad (9)$$

The resulting diesel/kerosene mixture has a concentration of 20 ppb (w/w) of Taggant #1 and 20 ppb (w/w) of Taggant #2.

Since Taggant #1 and Taggant #2 are the same taggants as used in Example 3, the resulting diesel has the same concentrations as Diesels 1, 2, and 3 measure in that example.

Using the instrument disclosed in U.S. Pat. No. 5,525,516, Diesels 1, 2, 3 were measured to have concentrations of 32.1 ppb, 32.7 ppb, and 31.3 ppb of taggant, respectively. Such measurements are 2.1 ppb. 2.7 ppb, and 1.3 ppb, respectively, from the 30 ppb of the undiluted diesel fuel tagged with Taggant #1. This is a percent difference of 6.5%, 8.3%, and 4.2%, respectively, from what would have been expected from measuring the undiluted diesel fuel tagged with Taggant #1. Given the tolerance of these measurements using such filtered photodiode detector, these results would wrongly determine the diesel fuel was not diluted. If this process is being used to authenticate the diesel fuel, this process would wrongly provide results indicating the diesel fuel was authentic, when, in fact, it was not. As used herein, a fuel or other liquid is "authentic" when that fuel or other liquid has not been changed, diluted, or otherwise adulterated. As also used herein, fuel or other liquid is "authenticated" when the method used to analyze the fuel or other liquid provides results that indicate the fuel or other liquid is authentic.

Using the multivariate analysis technique described by the present invention in the same manner as described above in Example 3, Diesels 1, 2, and 3 were measured to have concentrations of: (a) 20.8 ppb, 19.2 ppb, and 20.5 ppb, respectively, of Taggant #1; and (b) 19.4 ppb, 21.6 ppb, and 18.4 ppb, respectively, of Taggant #2. These results would reflect that the diesel tagged with Taggant #1 was measured to have been diluted in Diesel 1, 2, and 3 by a dilution percentage of 44.2%, 56.3%, and 46.3%, respectively, which are each close to the actual 50% dilution percentage of the diesel tagged with Taggant #1.

These dilution percentages of Diesels 1, 2, and 3 reflect that the diesel tagged with Taggant #1 was mixed with the diluting agent (or diluting agents) at ratios of 69/31, 64/36, and 68/32, respectively. These ratios are also close to the actual 67/33 (i.e., 2/1) of diesel tagged with Taggant #1 and the diluting agent (kerosene tagged with Taggant #2).

Moreover, if it is assumed that there was only one diluting agent (which contained Taggant #2), equation (8) can be utilized to determine the initial concentration of Taggant #2 from the final measured concentration (for the diluting agent) and the ratio of final volume to initial volume (of the diluting agent), as shown in equation (10).

$$\text{Initial } Conc = \text{Final } Conc \times \frac{\text{Final Volume}}{\text{Initial Volume}} \quad (10)$$

The measured concentrations of Taggant #2 in the diluting agent (the kerosene) for Diesels 1, 2, and 3 reflect concentrations of Taggant #2 in the original diluting agent of 63.3 ppb, 60.0 ppb, and 58.1 ppb, which are each close to the actual 60 ppb concentration of Taggant #2 in the kerosene. In some circumstances, the knowledge of the initial concentration of the diluting agent can assist in identifying the subsidized fuel that was used for dilution.

Example No. 5 Detection Of Marked Fuels Used As The Diluting Agent

The present invention can also be used to determine whether a fuel has been adulterated by diluting it with a marked fuel. This could be the case where the marked fuel (marked with a known fluorescent taggant) is a subsidized fuel that is being mixed with the fuel (unmarked or marked with a different fluorescent taggant) for sale at an increased price.

The analysis is thus to determine whether a known fluorescent taggant is present in a fuel, where none of that known fluorescence taggant should be. This occurs when the fuel marked with the known fluorescent taggant is used as the diluting agent. To insure that the known fluorescent taggant is present, the amount measured must be above some preset amount.

In such circumstance, the concentration typically is extremely low. For instance, if an unmarked fuel is diluted a marked fuel (having a taggant concentration of 20 ppb) at a ratio of 1:3 (one part unmarked fuel to 3 parts marked fuel), the resulting mixture would have a taggant concentration of 5 ppb. (The dilution percentage would be 300%).

At this concentration level, it would be difficult for the prior art devices to reliably detect the presence of the taggant (as this would be in the margin of error for such device) and even more difficult to achieve a reliable quantitative measurement. Suppose for example, the margin of error is ±6 ppb (which is shown in Table 1 and 3, above). Since the taggant concentration of Taggant #1 should be 0 ppb in the undiluted unmarked fuel, a measurement of 5 ppb would not indicate conclusively that the unmarked fuel was diluted.

With respect to using a marked fuel (marked with a known fluorescent taggant) as the diluting agent to dilute a marked fuel (having a different fluorescent taggant), Example 4 above reflects the problems that the prior art devices would have in detecting this dilution.

As before, the filtered photodiode detector would measure that Diesels 1, 2, 3 have concentrations of 32.1 ppb, 32.7 ppb, and 31.3 ppb of taggant, respectively. Again, given the tolerance of these measurements using such filtered photodiode detector, these results would wrongly determine the diesel fuel was not diluted.

However, the present invention would detect that Taggant #2 was present at concentrations of 19.4 ppb, 21.6 ppb, and 18.4 ppb, in Diesels 1, 2, and 3, respectively. As the amount of Taggant #2 should have been zero, such measurements reflect that dilution using the a marked fuel (marked with Taggant #2) is present (and, as noted above in Example 4, has been used to dilute the fuel at a 50% dilution percent. Accordingly, the present invention can reliably detect the presence of the taggant (as it would not be within the margin of error for such device) and would be able to achieve a reliable quantitative measurement.

Accordingly, described herein is a device, e.g., fluorometer, for detection of fluorescence from taggants in a liquid sample, specifically a liquid hydrocarbon, particularly a fuel; more particularly, there is described herein a design of a portable field-operated fluorometer for the detection of fluorescent taggants in a liquid petroleum matrix. The device suitably has an excitation source, which may be a laser or light emitting diode, and a CCD array may serve as the detector. This array provides a high resolution fluorescence emission spectrum of the fluorescent taggant and its fuel matrix. The entire optical assembly may be thermally stabilized, e.g., by a Peltier heater/cooler, which allows for an expanded ambient operating temperature ranges. The Peltier additionally serves to regulate the temperature of the sample vial, thus minimizing variations of fluorescence quantum yield of the taggant resulting from thermal changes.

Also disclosed is a method for improved determinations of a fluorescent taggant in a liquid sample, e.g., a liquid hydrocarbon matrix, that utilizes a background subtraction process and/or a multivariate process for such improved determinations.

The background subtraction process dynamically fits the background sample, e.g., hydrocarbon, fluorescence of an unknown sample based on the described mathematical model. Upon subtraction of the fluorescence contributions from the sample (e.g., hydrocarbon) matrix, the remaining fluorescence signal (now completely due to a chemical taggant) is accurately quantified by traditional means such as spectral integration. This process allows for the accurate quantification of taggants in a range of liquids, e.g., fuels, where the native background fluorescence is widely variable.

The second process for use in the present invention and that will result in improved quantification of a florescent taggant in a liquid sample, e.g., petroleum matrix, employs a multivariate analysis. For this process, a training set composed of the taggant in a wide range of solvent environments is used to generate a calibration model using a partial least squares (or similar) regression analysis. The calibration model is then used to accurately predict taggant concentrations of unknown samples. This method allow for taggants susceptible to significant solvatochromic shifting to more accurately be quantified.

Figure 6:
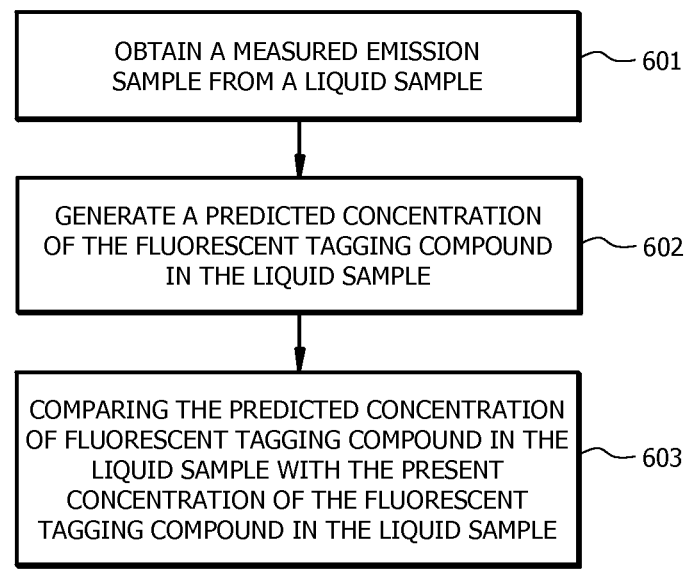
FIG. 6 illustrates a flow diagram of an embodiment of a method in accordance with the present invention.

FIG. 6 illustrates a flow diagram of an embodiment of a method in accordance with aspects of the present invention. In step 601, a measured emission spectrum is obtained from a liquid sample. To do so, the liquid sample can be exposed to a light source that causes a fluorescent tagging compound in the liquid sample to fluoresce over a spectral range. In step 602, a predicted concentration of the fluorescent tagging compound in the liquid sample is generated using the measured emission spectrum. The generating includes using one or both of the background subtraction process and the multivariate process. In step 603, the predicted concentration of the fluorescent tagging compound in the liquid sample is compared to a preset concentration of the fluorescent compound in the liquid sample.

Devices disclosed herein afford a full fluorescence emission spectrum of the sample to be obtained, as opposed to other, e.g., portable, fluorescence systems based on one or a couple of filtered photodiodes. In a filtered photodiode-based system, light be it from background sample (e.g., fuel) fluorescence or taggant signal looks the same to the device, as such quantification in fuels of variable backgrounds becomes very inaccurate. Similarly, as the solvent environment of a fluorophore changes from liquid to liquid, as in the case of from fuel to fuel (e.g., gasoline to diesel fuel), the fluorescence spectrum changes as well; filtered photodiode based instrumentation is incapable of detecting this change and again becomes less accurate. Embodiments of the present invention overcome both of these limitations by being able to capture a full emission spectrum of the sample. Because of this dramatically increased amount of sample information, background fluorescence from the sample can be modeled and removed as described by the disclosed method. Similarly, with a full emission spectrum of the sample, a multivariate analysis may be performed allowing for the solvatochromic effects (spectral changes due to changing solvent environment) to be minimized as well.

Fluorescence based taggants in general afford advantages of absorption based systems as a result of the lower taggant treat rates necessary for detection. Because less taggant is added, the fuel and the innate properties of the fuel (combustion properties, fuel color, etc.) will change less, and the same applies to liquids other than fuels. Fluorescence based taggants can also have a dramatic financial advantage over absorption based taggants, since a substantially lower treat rate leads to substantially lower treat costs per volume of fuel or other liquid marked.

Figure 7:
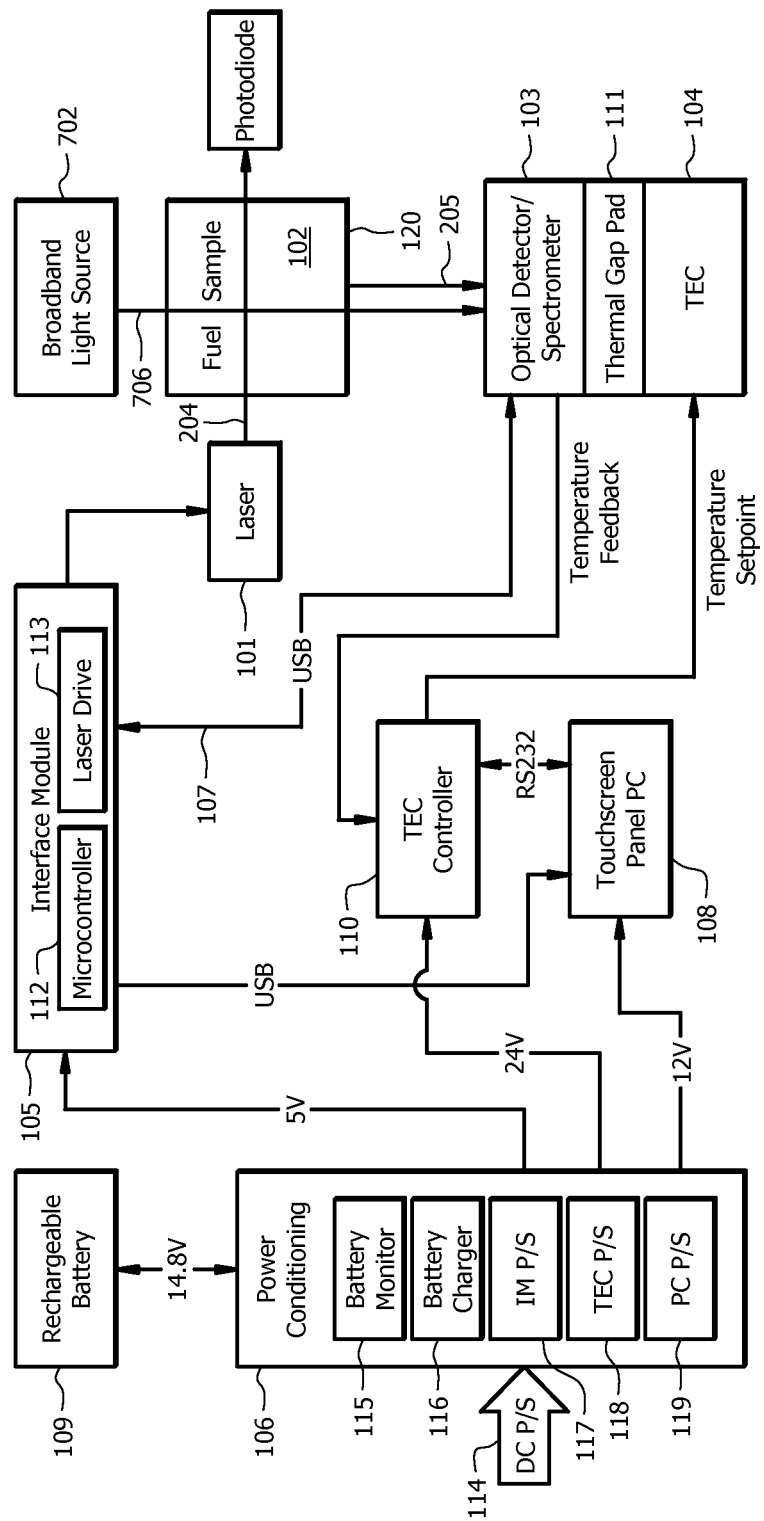
FIG. 7 is a schematic diagram of another embodiment of a fluorescence spectrometer.

FIG. 7 is a schematic diagram of another embodiment of a fluorescence spectrometer 700. Fluorescence spectrometer 700 is configured to provide an excitation light 204 to a liquid sample (e.g., fuel sample 102), to provide a broadband light 706 across the liquid sample, to detect an emission light 205 from the liquid sample in response to providing the excitation light 204 and the broadband light 706, and to analyze the emission light 205 and broadband light 706. An example of a liquid sample includes, but is not limited to, a fuel sample. Fluorescence spectrometer 700 is configured similarly to fluorescence spectrometer 100 in FIG. 1. Fluorescence spectrometer 700 may be configured as shown or in any other suitable manner.

Fluorescence spectrometer 700 comprises a laser 101 that is configured to emit the excitation light 204 through the fuel sample 102 and orthogonal to the optical detector 103. Fluorescence spectrometer 700 further comprises a broadband light source 702 and a photodiode 704. The broadband light source 702 is configured to emit the broadband light 706 across fuel sample 102 and to the optical detector 103. The broadband light 706 may be used to determine an absorbance of the liquid sample 102. Broadband light 706 has a broad optical bandwidth, for example, an optical bandwidth of 100 nm or more. Broadband light 706 may comprise wavelengths within and/or outside of the visible light spectrum. Examples of a broadband light source 702 include, but are not limited to, a white light source and a light emitting diode (LED).

Photodiode 704 is configured to detect at least a portion of the excitation light 204 and to generate an electrical signal in response to the detected the excitation light 204. Photodiode 704 measures the intensity of the excitation light and may determine an absorption at the laser 101. The intensity of the excitation light and/or the absorption at the laser 101 may be used for processes such as correcting a spectrum or classifying a spectrum. Photodiode 704 may be any suitable number of or type of photodetectors that are capable of detecting the excitation light 204.

Optical detector 103 is configured to detect and measure the emission light 205 that is emitted from the fuel sample in response to providing the excitation light 204 from the laser 101 to the fuel sample 102. Optical detector 103 is also configured to detect the absorbance from the broadband light 706 that is emitted from the broadband light source 702. The detected emission light 205 and the absorbance from the broadband light 706 may be used for processes to improve the classification or quantification of fuel sample 102. In an embodiment, the emission light 205 and the absorbance from the broadband light 706 are detected or processed sequentially nearly simultaneously. For example, the emission light 205 may be detected before the absorbance from the broadband light 706 is detected or vice-versa.

Figure 8:
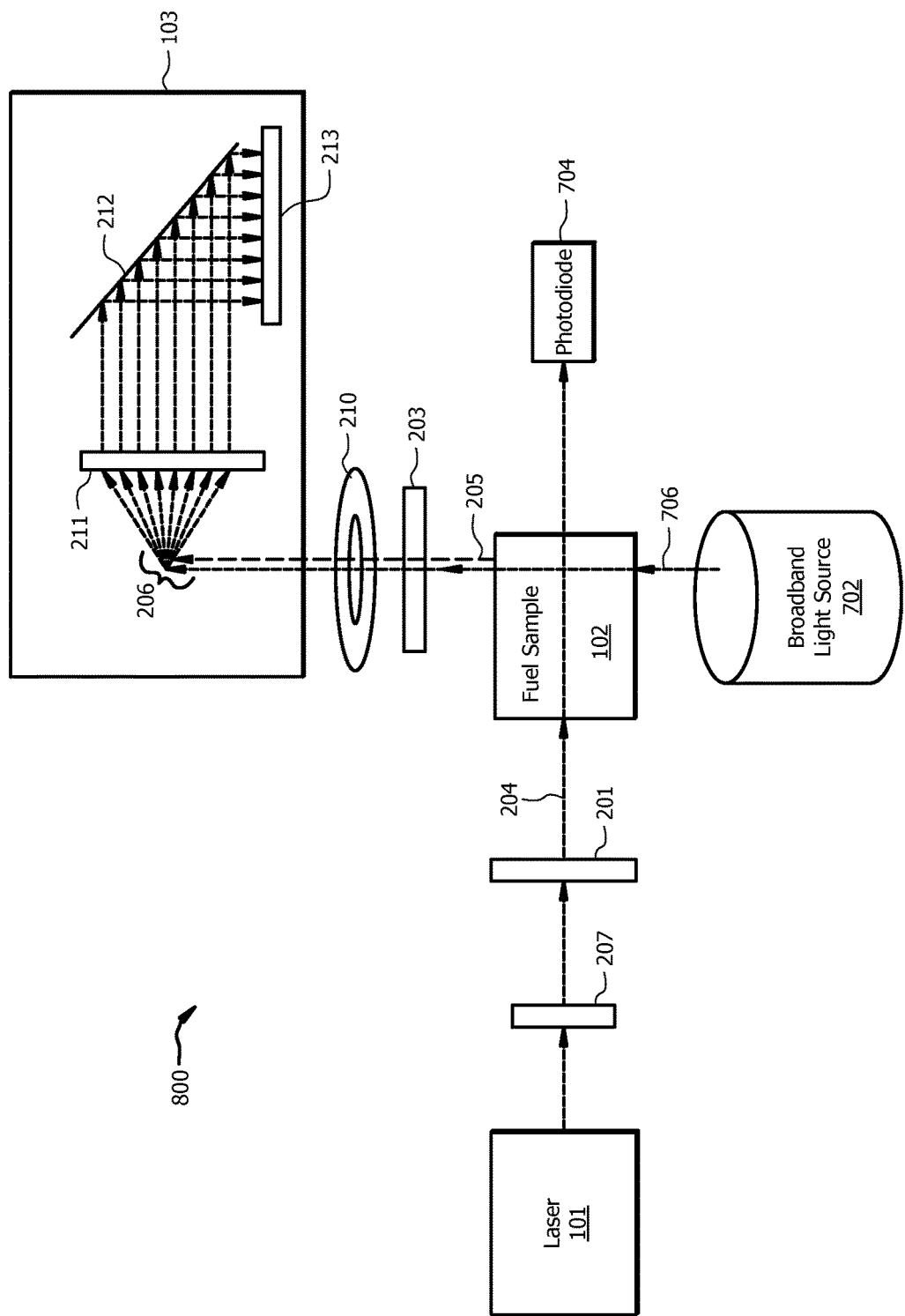
FIG. 8 is a schematic diagram of another embodiment of optical elements that can be used in a fluorescence spectrometer.

FIG. 8 is a schematic diagram of another embodiment of optical elements 800 that can be used in a fluorescence spectrometer such as fluorescence spectrometer 700 in FIG. 7. Optical elements 800 comprises laser 101, lens 207, short-pass optical filter 201, broadband light source 702, photodiode 704, long-pass optical filter 203, fixed slit 210, and optical detector 103. Optical elements 800 may be configured as shown or in any other suitable manner.

Laser 101 is configured to emit an excitation light 204 through the lens 207 and the short-pass optical filter 201 to fuel sample 102. At least a portion of the excitation light 204 also passes to photodiode 704. Photodiode 704 is configured to detect at least a portion of the excitation light 204 and to generate an electrical signal in response to the detected the excitation light 204. Photodiode 704 measures the intensity of the excitation light and may determine an absorption at the laser 101. The intensity of the excitation light and/or the absorption at the laser 101 may be used for processes such as correcting a spectrum or classifying a spectrum. The fuel sample 102 is configured to receive the excitation light 204 and to emit an emission light 205 in response to receiving the excitation light 204.

Broadband light source 702 is configured to emit a broadband light 706 across fuel sample 102 to the optical detector 103. Broadband light source 702 and broadband light 706 are similar as described in FIG. 7.

The emission light 205 and the broadband light 706 pass through the long-pass optical filter 203 and the fixed slot 210 to the optical detector 103. Optical detector 103 comprises a collimating mirror 206, a diffraction grating 211, a focusing mirror 212, and detector elements 213. Optical detector 103 may be configured similar to optical detector 103 in FIG. 2. Optical detector 103 is configured to detect and measure the emission light 205 and an absorbance from the broadband light 706. In an embodiment, optical detector 103 is further configured to discriminate different wavelengths of light using any suitable components or methods as would be appreciated by one of ordinary skill in the art upon viewing this disclosure. The detected emission light 205 and the absorbance from the broadband light 706 may be used for processes to improve the classification or quantification of fuel sample 102. In an embodiment, the emission light 205 and the absorbance from the broadband light 706 are detected or processed sequentially nearly simultaneously. For example, the emission light 205 may be detected before the absorbance from the broadband light 706 is detected or vice-versa.

Figure 9:
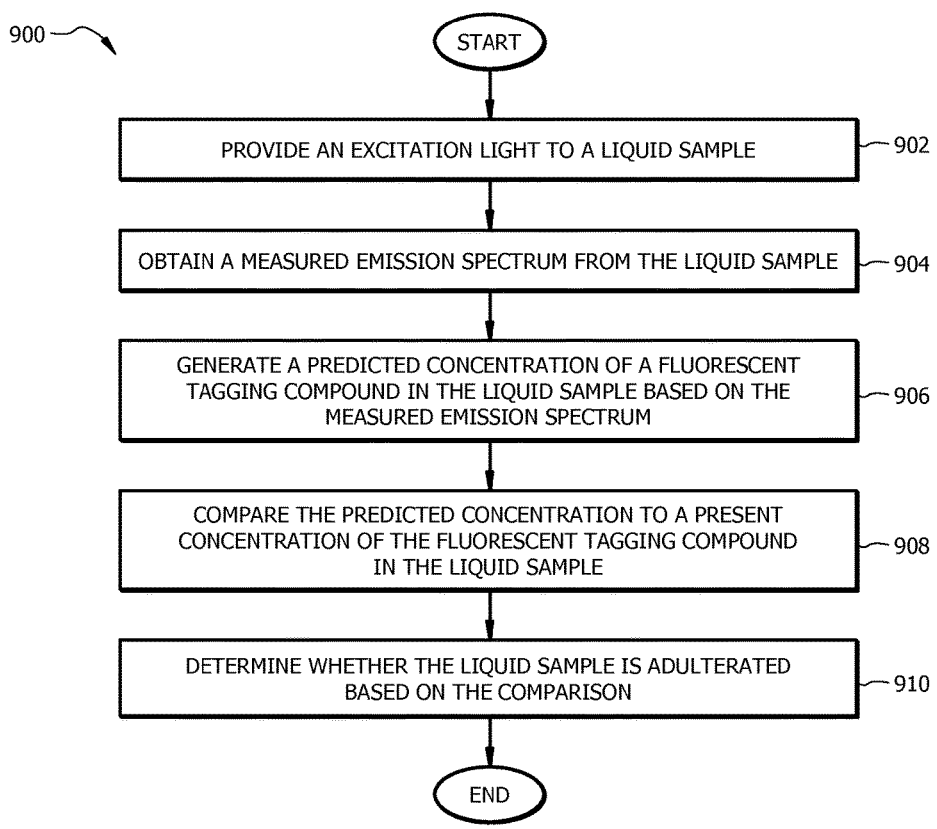
FIG. 9 is a flowchart of an embodiment of a liquid sample analysis method.

FIG. 9 is a flowchart of an embodiment of a liquid sample analysis method 900. Method 900 is implemented in a fluorescence spectrometer to determine whether a liquid sample comprises a particular fluorescent tagging compound at a preset concentration. The fluorescence spectrometer may employ method 900 to detect fuel dilution or adulteration using fluorescent tagging compounds. The fluorescence spectrometer is configured similarly to fluorescence spectrometer 700 in FIG. 7.

At step 902, the fluorescence spectrometer provides an excitation light to a liquid sample. The excitation light may be similar to excitation light 204 and the broadband light may be similar to broadband light 706 in FIG. 7, respectively. Exposure to the excitation light causes fluorescent tagging compounds in the liquid sample to fluoresce over a spectral range. For example, a spectral range may comprise a range from about 600 nm to about 1100nm, from about 650 nm to about 950 nm, from about 700 nm to about 900nm, or any other suitable spectral range as would be appreciated by one of ordinary skill in the art upon viewing this disclosure. The use of the term "about" means ±10% of the subsequent number, unless otherwise stated.

At step 904, the fluorescence spectrometer obtains a measured emission spectrum from the liquid sample in response to providing the excitation light. For example, an optical detector detects an emission light from liquid sample and generates measured emission spectrum in response to detecting the emission light. The optical detector may be configured similar to optical detector 103 in FIG. 2.

At step 906, the fluorescence spectrometer generates a predicted concentration of a fluorescent tagging compound in the liquid sample based on the measured emission spectrum. The fluorescence spectrometer may perform a quantitative analysis to generate the predicted concentration of the fluorescent tagging compound. Examples of quantitative analysis include, but are not limited to, performing a multivariate analysis and performing a background subtraction analysis. A multivariate analysis can be performed on the measured emission spectrum similar to previously described. For example, a multivariate analysis may comprise selecting a library or a model stack that comprises known emission spectra that are each correlated to a known concentration of a particular fluorescent tagging compound and using the library and the measured emission spectrum to generate a predicted concentration of a particular fluorescent tagging compound in the liquid sample.

A background subtraction analysis can be performed on the measured emission spectrum similar to previously described. For example, a background subtraction analysis may comprise determining a background emission spectrum from the measured emission spectrum, removing or substantially reducing the background emission from the measured emission spectrum to generate a predicted emission spectrum, and evaluating the predicted emission spectrum to generate a predicted concentration of a particular fluorescent tagging compound in the liquid sample.

At step 908, the fluorescence spectrometer compares the predicted concentration of the fluorescent tagging compound in the liquid sample to a preset concentration of the fluorescent tagging compound in the liquid sample. Comparing the predicted concentration to the preset concentration allows the fluorescence spectrometer to detect fuel dilution or adulteration using the fluorescent tagging compounds.

At step 910, the fluorescence spectrometer determines whether the liquid sample is adulterated or diluted based on the comparison of the predicted concentration of the fluorescent tagging compound in the liquid sample to the preset concentration of the fluorescent tagging compound in the liquid sample.

Figure 10:
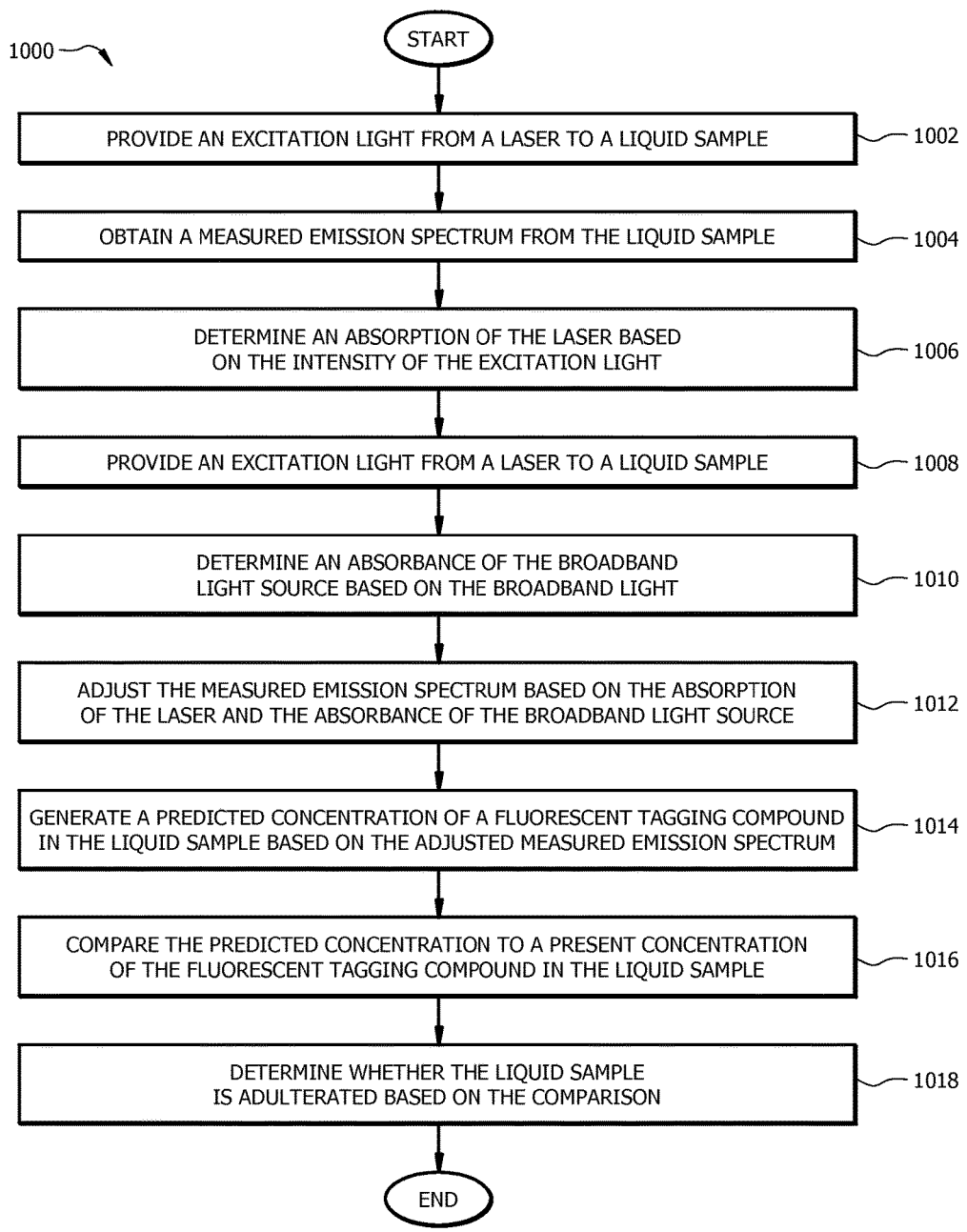
FIG. 10 is a flowchart of another embodiment of a liquid sample analysis method.

FIG. 10 is a flowchart of another embodiment of a liquid sample analysis method 1000. Method 1000 is implemented in a fluorescence spectrometer to determine whether a liquid sample comprises a particular fluorescent tagging compound at a preset concentration. The fluorescence spectrometer may employ method 1000 to detect fuel dilution or adulteration using fluorescent tagging compounds. The fluorescence spectrometer is configured similarly to fluorescence spectrometer 700 in FIG. 7.

At step 1002, the fluorescence spectrometer provides an excitation light from a laser to a liquid sample. The excitation light may be similar to excitation light 204 and the laser may be similar to laser 101 in FIG. 7, respectively. Exposure to the excitation light causes fluorescent tagging compounds in the liquid sample to fluoresce over a spectral range.

At step 1004, the fluorescence spectrometer obtains a measured emission spectrum from the liquid sample in response to providing the excitation light. For example, an optical detector detects an emission light from liquid sample and generates measured emission spectrum in response to detecting the emission light. The optical detector may be configured similar to optical detector 103 in FIG. 2.

At step 1006, the fluorescence spectrometer determines an absorption of the laser based on the intensity of the excitation light. The intensity of the excitation light may indicate how much the liquid sample modulates the measured emission spectrum at the excitation wavelengths.

At step 1008, the fluorescence spectrometer provides a broadband light from a broadband light source to the liquid sample. The broadband light may be similar to broadband light 706 and the broadband light source may be similar broadband light source 702 in FIG. 7, respectively.

At step 1010, the fluorescence spectrometer determines an absorbance of the broadband light source based on the broadband light.

At step 1012, the fluorescence spectrometer adjusts the measured emission spectrum based on the absorption of the laser and the absorbance of the broadband light source. The fluorescence spectrometer may correct or compensate the measured emission spectrum based on the absorption of the laser and the absorbance of the broadband light source using an implicit correction or an explicit correction. An implicit correction may correct the effect of a sample absorbance on a fluorescence emission using variants of a PLS regression model. For example, an implicit correction may comprise concatenating the measured emission spectra and an absorbance spectra that is derived from the liquid sample and using the scaled combination spectra to model a marker or taggant concentration. This example of implicit correction may be employed for exploiting information content in the combined spectra to derive regression parameters that are orthogonal or uncorrelated with the liquid sample absorbance. Another example of implicit correction may comprise using the measured emission spectra and samples of an absorbance spectra that span the wavelength region across which the measured emission spectra is derived. This example of implicit correction may be employed to exploit the correlation structure between multiple dependent variables in order to stabilize the determination of the PLS regression parameters, which may be less sensitive to the influence of the liquid sample absorbance. Additional details for examples of implicit correction are described in, "Multi-Modal-Spectroscopy and Multivariate Data Analysis as a Tool for Non-Invasive Process Analysis," by Kessler, et al., published in 2013, and "Process Analytical Technology: Spectroscopic Tools and Implementation Strategies for the Chemical and Pharmaceutical Industries," published by John Wiley and Sons in 2010, which are both hereby incorporated by reference as if reproduced in their entirety. An explicit correction may correct the effect of a sample absorbance on a fluorescence emission using a mathematical model that describes the relationship between a fluorescence spectra and an absorbance spectra for a given optical geometry. For example, explicit correction may comprise using cross-illumination or a right-angled geometry similar to the configurations of the fluorescence spectrometer 700 in FIG. 7 and the optical elements 800 in FIG. 8. Additional details for examples of explicit correction are described in, "Improvement of Inner Filter Effect Correction Based on Determination of Effective Geometry Parameters Using a Conventional Fluorimeter," by Q. Gu, et al., published in 2009, and "Real-time compensation of the inner filter effect in high-density bioluminescent cultures," by K. B. Konstantinov, et al., published in 1993, which are hereby incorporated by reference as if reproduced in their entirety.

At step 1014, the fluorescence spectrometer generates a predicted concentration of a fluorescent tagging compound in the liquid sample based on the adjusted measured emission spectrum. The fluorescence spectrometer may perform a quantitative analysis or a background subtraction analysis to generate the predicted concentration of the fluorescent tagging compound. Generating a predicted concentration of a fluorescent tagging compound in the liquid sample based on the adjusted measured emission spectrum may be performed using a process similar to step 906 in FIG. 9.

At step 1016, the fluorescence spectrometer compares the predicted concentration of the fluorescent tagging compound in the liquid sample to a preset concentration of the fluorescent tagging compound in the liquid sample. Comparing the predicted concentration to the preset concentration allows the fluorescence spectrometer to detect fuel dilution or adulteration using the fluorescent tagging compounds.

At step 1018, the fluorescence spectrometer determines whether the sample is adulterated or diluted based on the comparison of the predicted concentration of the fluorescent tagging compound in the liquid sample to the preset concentration of the fluorescent tagging compound in the liquid sample.

Figure 11:
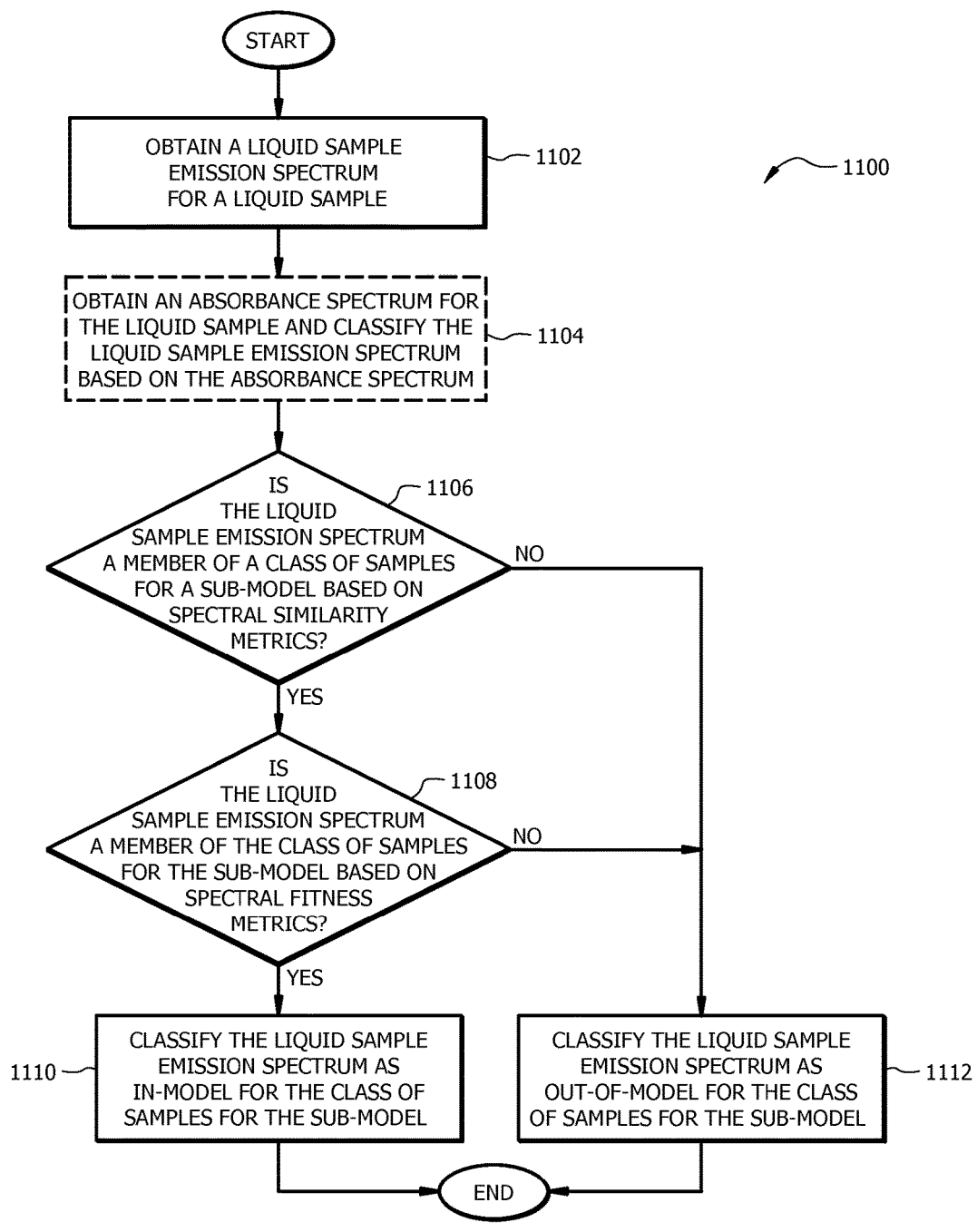
FIG. 11 is a flowchart of an embodiment of a liquid sample emission spectrum classification method.

FIG. 11 is a flowchart of an embodiment of a liquid sample emission spectrum classification method 1100. Method 1100 is implemented in a fluorescence spectrometer to classify a liquid sample emission spectrum based on spectral similarity and spectral fitness to a sub-model in a model stack. A sub-model is a quantitative or semi-quantitative model that is defined for a known class of fuel samples. For example, a sub-model is a quantitative model when the sub-model is associated with an exclusive flag and the sub-model is a semi-quantitative model when the sub-model is associated with an inclusive flag. An example of a sub-model includes, but is not limited to, a PLS model. A model stack comprises one or more models or sub-models that are associated with a specific sub-group of a fuel type, for example, gasoline or diesel. The fluorescence spectrometer may employ method 1100 for classifying liquid sample emission spectrum to be used in a multivariate analysis for a liquid sample analysis method such as liquid sample analysis method 900 in FIG. 9 and liquid sample analysis method 1000 in FIG. 10. The fluorescence spectrometer is configured similarly to fluorescence spectrometer 700 in FIG. 7.

At step 1102, the fluorescence spectrometer obtains a liquid sample emission spectrum. For example, the fluorescence spectrometer may provide an excitation light to a liquid sample and an optical detector may detect an emission light from liquid sample and generate the liquid sample emission spectrum in response to detecting the emission light. As an example, the liquid sample may be a fuel sample acquired from a gas station in a particular region.

Optionally at step 1104, the fluorescence spectrometer obtains an absorption spectrum and classifies the liquid sample emission spectrum based on the absorption spectrum. The absorption spectrum may comprise an absorption of a laser or an absorbance of a broadband light source. The fluorescence spectrometer may classify the liquid sample as a high-absorbing sample or a low-absorbing sample based on the absorbance spectrum. Additionally or alternatively, the fluorescence spectrometer may map the absorbance spectrum and the liquid sample emission spectrum and use the relationship between the absorbance spectrum and the liquid sample emission spectrum for classification. In an embodiment, the absorption spectrum may be used for classification based on spectral similarity metrics and spectral fitness metrics similar to steps 1106-1112.

At step 1106, the fluorescence spectrometer determines whether the liquid sample emission spectrum is a member of a class of samples based on spectral similarity metrics for a sub-model in a model stack. A spectral similarity metric may comprise a discriminant function that can be defined in principle component (PC) space for classifying sub-models by similar types and/or properties. A type refers to a fuel type. Examples of fuel types include, but are not limited to, gasoline, diesel, kerosene, lubricants, and gas oil. Properties refers to chemical or physical properties of fuel blends that result in distinctive fluorescent and/or absorbance spectra from which fuel classifiers can be derived. Additional details for a PC space are described in, "Discriminant Analysis of Principal Components for Face Recognition," by W. Zhao, et al., published in April 1998, which is hereby incorporated by reference as if reproduced in its entirety.

Any suitable number of PC dimensions may be used to define spectral similarity metrics for a class of samples in a sub-model. For example, a 2-dimensional (2D) PC space or a 3-dimensional (3D) PC space may be used to define spectral similarity metrics for classes of samples in sub-models. The discriminant function defines geometric shapes across PC spaces that are associated with classes of samples for discriminating the liquid sample emission spectrum with respect to the classes of samples. Examples of geometric shapes for classes of samples include, but are not limited to, lines, planes, ellipses, and ellipsoids. Geometric shapes can be described using algebraic parameters that are coefficients for the PC space. For example, algebraic parameters for a 3D PC space are $X^2$, $Y^2$, $Z^2$, $X \cdot Y$, $X \cdot Z$, $Y \cdot Z$, $X$, $Y$, $Z$, and $1$, where $X$, $Y$, and $Z$ are the dimensional axis of the 3D PC space. An ellipse is defined in 2D PC space using the following equation:

$$\frac{x^2}{a^2} + \frac{y^2}{b^2} = 1$$

and an ellipsoid is defined in 3D PC space using the following equation:

$$\frac{x^2}{a^2} + \frac{y^2}{b^2} + \frac{z^2}{c^2} = 1$$

where a, b, and c are the radii along the x-, y-, and z-dimension, respectively. In an embodiment, the boundaries of a geometric shape can be derived based on one or more sub-models or can be defined manually.

The bounds of geometric shapes are used to define a membership for a class of samples. The liquid sample emission spectrum is projected onto the geometric shape to determine whether the liquid sample emission spectrum is located at the surface of a geometric shape, inside the geometric shape, or outside of the geometric shape. For example, a liquid sample emission spectrum in a 3D PC space is represented as a point (x, y, z). Projecting the location of the liquid sample emission spectrum relative to a geometric shape can be performed by evaluating the following expression:

$$f = V^T R$$

where V represents the algebraic parameters and R represents a vector [$x^2$, $y^2$, $z^2$, x·y, x·z, y·z, x, y, z] for the liquid sample emission spectrum. When f equals one or is greater than one, the liquid sample emission spectrum is either located on the surface of the geometric shape or is outside of the geometric shape in which case the sample does not belong to the class of samples defined by the geometric shape. When f is less than one, the liquid sample emission spectrum is enclosed within the geometric shape and is a member of the class of samples defined by the geometric shape. For geometric shapes in a 2D PC space, the terms associated with the third dimensional axis (e.g., dimension z) are set to zero. For example, a liquid sample emission spectrum in 2D PC space is represented by a point (x, y) and a vector [$x^2$, $y^2$, 0, x·y, 0, 0, x, y, 0]. The fluorescence spectrometer proceeds to step 1108 when the liquid sample emission spectrum is a member of the class of samples defined by the geometric shape; otherwise, the fluorescence spectrometer proceeds to step 1112.

At step 1108, the fluorescence spectrometer determines whether the liquid sample emission spectrum is a member of a class of samples based on a spectral fitness metric for the sub-model. A spectral fitness metric for determining whether the liquid sample emission spectrum is a member of a class of samples for the sub-model may comprise using a scale invariant sum of squared error metric that compares the liquid sample emission spectrum to the spectrum that is estimated by the sub-model. A spectrum fit $s_{est}$ to the sub-model can be calculated using the following:

$$s_{est} = s \cdot W \cdot P^T$$

where s represents the liquid sample emission spectrum that is a vector with a length equal to the number of wavelength channels n, W represents a matrix of spectrum weights, and P represents a matrix of spectrum loadings. The dimensions of matrices W and P are n×m, where m is the number of PC dimensions that describes the spectral space. The scaled sum of square error (SSSE) can be estimated using the following:

$$SSSE = \Sigma \left( \frac{s}{\sqrt{\Sigma s}} - \frac{s_{est}}{\sqrt{\Sigma s_{est}^2}} \right)^2.$$

An SSSE threshold is defined to determine when the liquid sample emission spectrum is included or excluded from the class of samples for the sub-model. For example, a liquid sample emission spectrum above the SSSE threshold is not a member of the class of samples for the sub-model. In an embodiment, the SSSE threshold may be manually defined, for example, based on one or more sub-models. The fluorescence spectrometer proceeds to step 1110 when the liquid sample emission spectrum is a member of the class of samples for the sub-model; otherwise, the fluorescence spectrometer proceeds to step 1112.

At step 1110, the fluorescence spectrometer classifies the liquid sample emission spectrum as in-model for the class of samples for the sub-model. When a liquid sample emission spectrum that is in-model for a class of samples in a sub-model, the liquid sample emission spectrum may be used in a multivariate analysis with the sub-model.

At step 1112, the fluorescence spectrometer classifies the liquid sample emission spectrum as out-of-model for the class of samples for the sub-model. When a liquid sample emission spectrum that is out-of-model for a class of samples in a sub-model, the liquid sample emission spectrum may not be used in a multivariate analysis with the sub-model.

Figure 12:
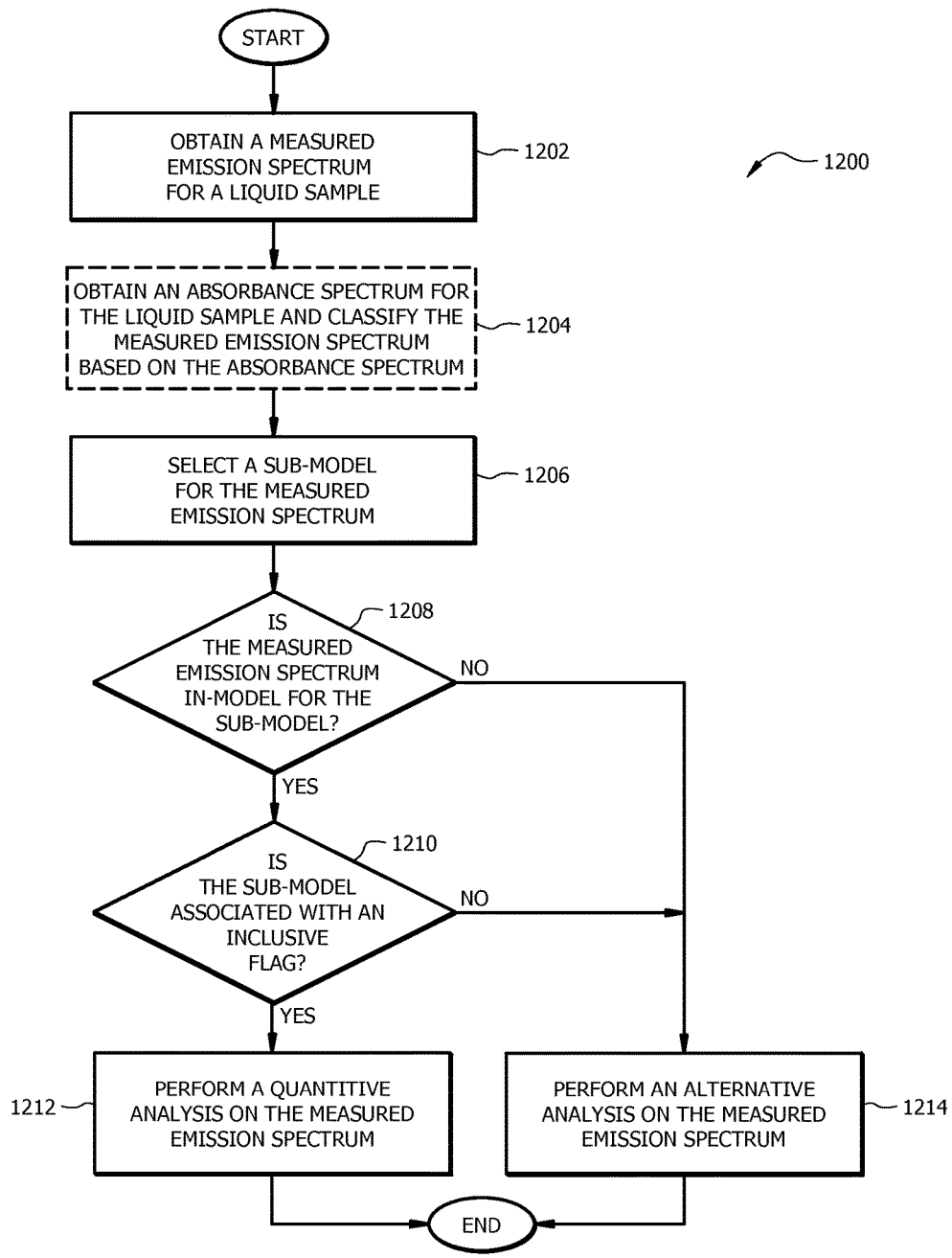
FIG. 12 is a flowchart of an embodiment of a liquid sample analysis method.

FIG. 12 is a flowchart of an embodiment of a liquid sample analysis method 1200. Method 1200 is implemented in a fluorescence spectrometer to determine whether a liquid sample comprises a particular fluorescent tagging compound at a preset concentration using a measured liquid emission for the liquid sample. When the measured emission spectrum is presented to a model stack (e.g., a fuel model stack) for a quantitative analysis (e.g., multivariate analysis), the sub-model that is selected for the measured emission spectrum is the first sub-model that describes the spectral space from which the measured emission spectrum was sourced. If there are N sub-models in the model stack and sub-models 1 to N−1 do not accurately describe the spectral space of the measured emission spectrum, then the $N^{th}$ or the last sub-model in the model stack may be automatically applied to the multivariate analysis of the measured emission spectrum. The fluorescence spectrometer may employ method 1200 for detecting fuel dilution or adulteration using fluorescent tagging compounds. The fluorescence spectrometer is configured similarly to fluorescence spectrometer 700 in FIG. 7.

At step 1202, the fluorescence spectrometer obtains a measured emission spectrum, for example, in responds to providing an excitation light to a liquid sample. An optical detector may detect an emission light from liquid sample and generate the measured emission spectrum in response to detecting the emission light.

Optionally at step 1204, the fluorescence spectrometer obtains an absorption spectrum and classifies the measured emission spectrum based on the absorption spectrum. The absorption spectrum may comprise an absorption of a laser or an absorbance of a broadband light source. The fluorescence spectrometer may classify the liquid sample as a high-absorbing sample or a low-absorbing sample based on the absorbance spectrum. Additionally or alternatively, the fluorescence spectrometer may map the absorbance spectrum and the liquid sample emission spectrum and use the relationship between the absorbance spectrum and the liquid sample emission spectrum for classification. In an embodiment, the absorption spectrum may be used for classification based on spectral similarity metrics and spectral fitness metrics similar to steps 1106-1112 in FIG. 11.

At step 1206, the fluorescence spectrometer selects a sub-model to compare to the measured emission spectrum. For example, the fluorescence spectrometer selects or obtains a sub-model from a model stack in a sequential order.

At step 1208, the fluorescence spectrometer determines whether the measured emission spectrum is in-model for the sub-model. Determining whether the measured emission spectrum is in-model for the sub-model may be performed using a liquid sample emission spectrum classification method similar to liquid sample emission spectrum classification method 1100 in FIG. 11. The fluorescence spectrometer proceeds to step 1210 when the measured emission spectrum is in-model for the sub-model; otherwise, the fluorescence spectrometer proceeds to step 1214 when the measured emission spectrum is out-of-model for the sub-model.

At step 1210, the fluorescence spectrometer determines whether the sub-model is associated with an inclusive flag. The sub-model may be associated with either an inclusive flag or an exclusive flag. An inclusive flag or an exclusive flag may be predetermined and stored as part of the model configuration parameters. Sub-models that are associated with an inclusive flag can be trusted to provide an accurate estimate of a marker concentration level and an estimate from which the quality (e.g., fuel quality) can be assessed, for example, to determine if the quality of a liquid sample passes, fails, or is suspicious. Sub-models that are associated with an exclusive flag indicate that a sub-model may not be trusted to provide an accurate estimate of marker concentration. For example, a sub-model may be associated with an exclusive flag because of marker variations in the samples that define the sub-model space and/or because the number of samples that make up the fuel space does not allow for an accurate quantitative analysis. The fluorescence spectrometer proceeds to step 1212 when the sub-model is associated with inclusive flag; otherwise, the fluorescence spectrometer proceeds to step 1214 when the sub-model is associated with an exclusive flag.

At step 1212, the fluorescence spectrometer performs a quantitative analysis on the measured emission spectrum. For example, the fluorescence spectrometer may perform a multivariate analysis using the measured emission spectrum and the sub-model.

At step 1214, the fluorescence spectrometer performs an alternative analysis on the measure emission spectrum. In an embodiment, the fluorescence spectrometer may determine whether the measured emission spectrum can be assessed using a quantitative analysis with the sub-model, for example, based on rough estimates of marker levels. In another embodiment, the measured emission spectrum may be set aside for a supplementary analysis. In an embodiment, a supplementary analysis may comprise laboratory methods that can be applied to fuel samples for verifying out-of-model results from the fluorescence spectrometer. Examples of laboratory methods include, but are not limited to, Gas Chromatography-Mass Spectrometry (GC-MS) and High Performance Liquid Chromatography (HPLC).

Figure 13:
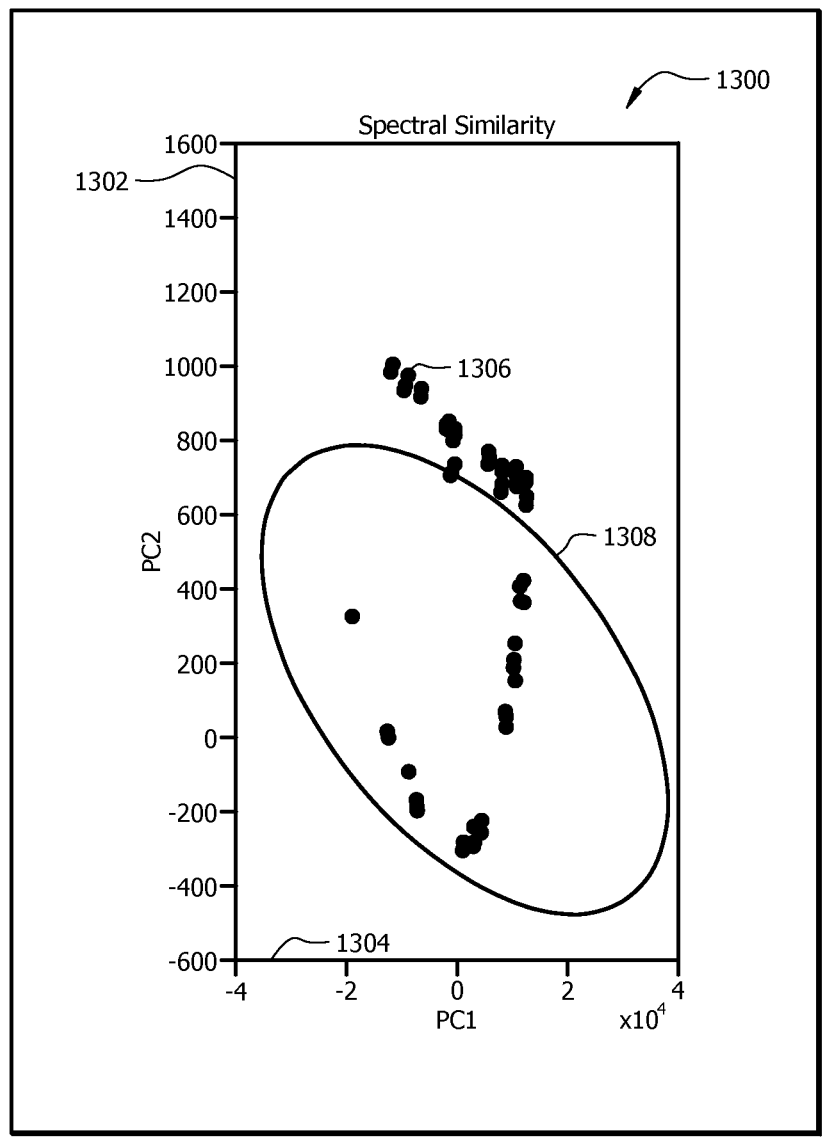
FIG. 13 is a graph of an embodiment of spectral similarity mapping.

FIG. 13 is a graph 1300 of an embodiment of spectral similarity mapping. A spectral similarity mapping may be used to determine whether a liquid sample emission spectrum is a member of a class for a sub-model in a model stack based on spectral similarity metrics. Axis 1304 represents a relative position with respect to a first PC space dimension which may correspond with spectral intensity variation across all wavelength channels and axis 1302 represents a relative position with respect to a second PC space dimension which may correspond with spectrum shape variations across all wavelength channels. Emission spectrums are represented as points 1306. Geometric shape 1308 is an ellipse that is used for discriminating the liquid sample emission spectrum with respect to class of samples. For example, when a point 1306 that corresponds with the liquid sample emission spectrum is located at the surface of or outside of geometric shape 1308, the liquid sample emission spectrum not a member of the class of samples. When a point 1306 that corresponds with the liquid sample emission spectrum is enclosed within geometric shape 1308, the liquid sample emission spectrum is a member of the class of samples.

Figure 14:
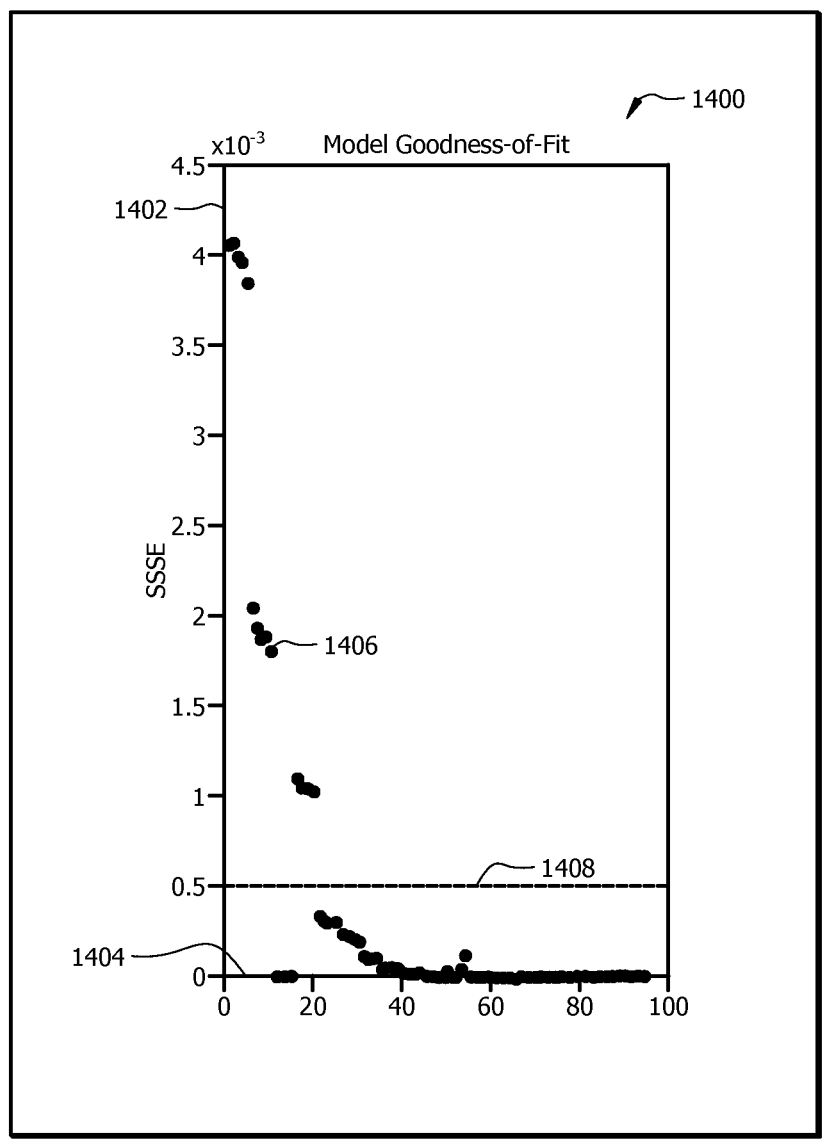
FIG. 14 is a graph of an embodiment of a spectral fitness mapping.

FIG. 14 is a graph 1400 of an embodiment of a spectral fitness mapping. A spectral fitness mapping may be used to determine whether a liquid sample emission spectrum is a member of a class for a sub-model in a model stack based on spectral fitness metrics. Axis 1404 represents a relative position with respect to a first PC space dimension and axis 1402 represents SSSE levels. Emission spectrums are represented as points 1402. SSSE threshold 1408 is used for discriminating the liquid sample emission spectrum with respect to a class of samples. For example, when a point 1406 that corresponds with the liquid sample emission spectrum is located above the SSSE threshold 1408, the liquid sample emission spectrum not a member of the class of samples.

Figure 15:
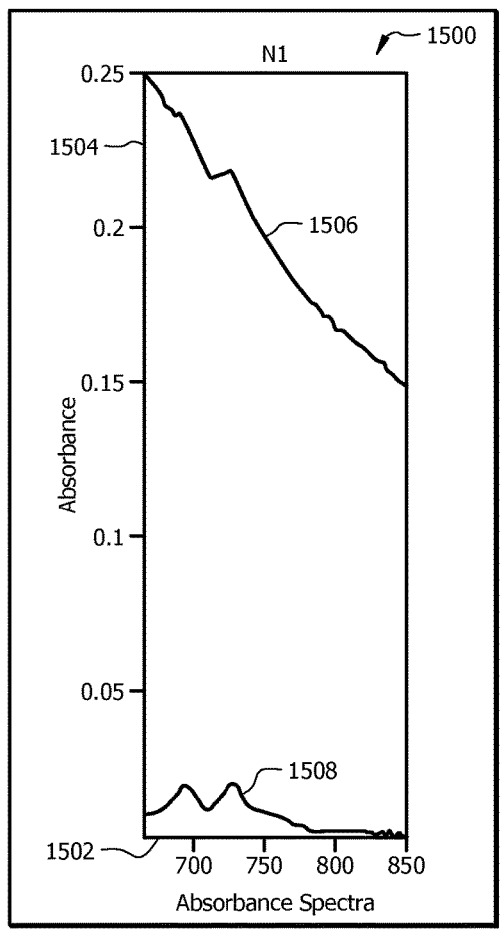
FIG. 15 is a graph of an embodiment of an absorbance spectrum for two fuels that are dosed with a quantum photonic marker.

FIG. 15 is a graph 1500 of an embodiment of an absorbance spectrum for two fuels that are dosed with a quantum photonic marker. An absorbance spectrum may be used to measure the amount of absorbance for a fuel dosed with the quantum photonic marker over a range of wavelengths of light. Axis 1502 represents wavelengths of light for an absorbance spectra and axis 1504 represents absorbance levels. The absorbance spectra comprises wavelengths of light from about 650 nm to about 850 nm. Fuel 1506 may be referred to as a high absorbing fuel with an absorbance that varies between about 0.25 and about 0.15 over the absorbance spectra. Fuel 1508 may be referred to as a low absorbing fuel with an absorbance that varies between about 0.02 to about 0.0 over the absorbance spectra.

One of ordinary skill in the art would appreciate that all of the classifications described here based on the liquid sample emission spectrum may also be performed using a liquid sample absorption spectrum as an input to a classification routine such as method 900 in FIG. 9, method 1000 in FIG. 10, method 1100 in FIG. 11 and method 1200 in FIG. 12. The liquid sample absorption spectrum may be used in addition to the liquid sample emission spectrum or as an alternative to the liquid sample emission spectrum. Therefore, near simultaneous measurements of the emission and absorption spectra can give to possible routes to classifying the liquid sample for further analysis.

Figure 16:
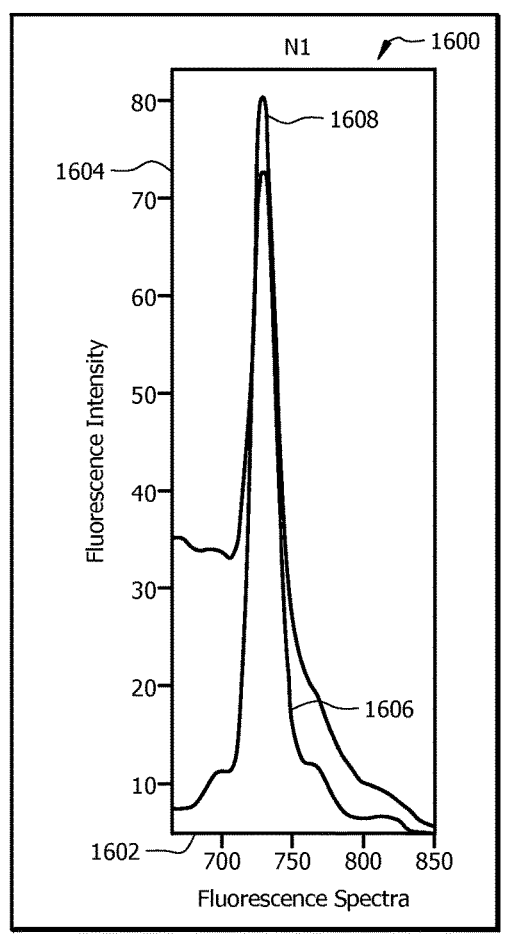
FIG. 16 is a graph of an embodiment of a fluorescence spectrum without absorbance correction for two fuels that are dosed with a quantum photonic marker.

FIG. 16 is a graph 1600 of an embodiment of a fluorescence spectrum without absorbance correction for two fuels that are dosed with a quantum photonic marker. A fluorescence spectrum may be used to measure fluorescence intensity of a fuel dosed with the quantum photonic marker over a range of wavelengths of light. Axis 1602 represents wavelengths of light for a fluorescence spectra and axis 1604 represents fluorescence intensity levels. The fluorescence spectra comprises wavelengths of light from about 650 nm to about 850 nm. The quantum photonic marker and fuels correspond with the quantum photonic and fuels used to generate graph 1500 in FIG. 15. Fuel 1608 corresponds with a low absorbing fuel such as fuel 1508 in FIG. 15. Fuel 1606 corresponds with a high absorbing fuel such as fuel 1506.

Figure 17:
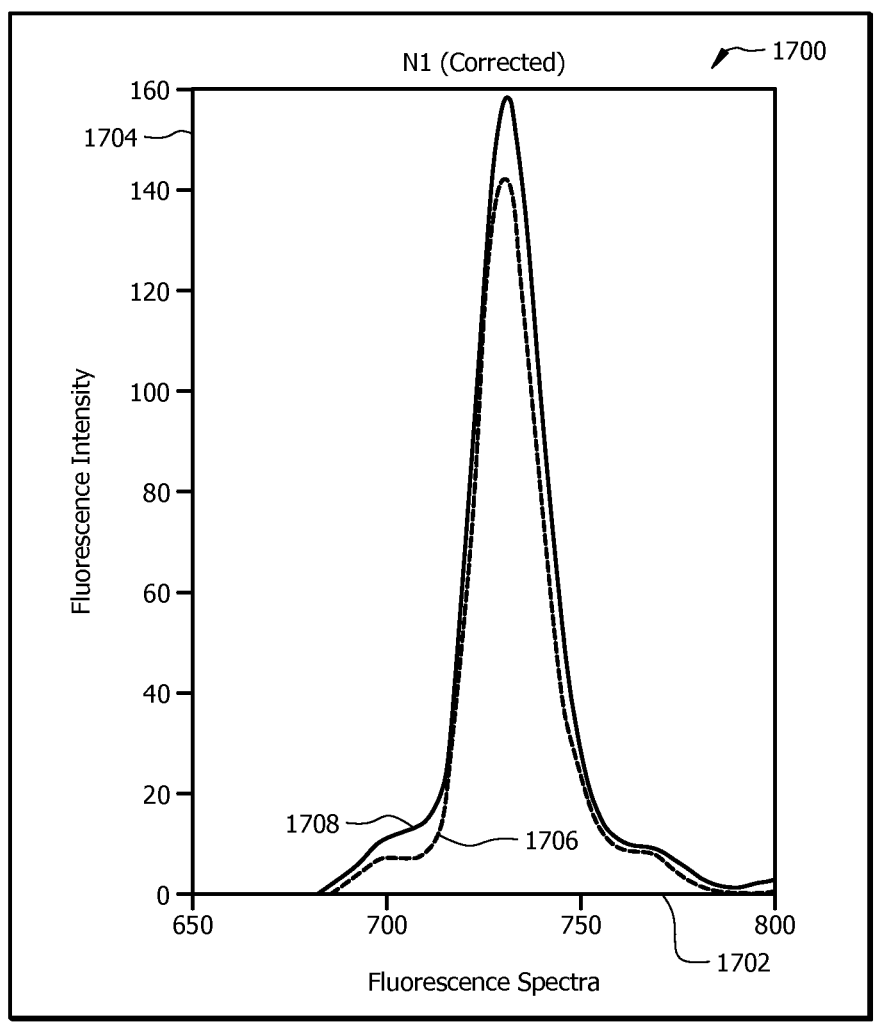
FIG. 17 is a graph 1700 of an embodiment of an absorbance corrected fluorescence spectrum for two fuels that are dosed with a quantum photonic marker.

FIG. 17 is a graph 1700 of an embodiment of an absorbance corrected fluorescence spectrum for two fuels that are dosed with a quantum photonic marker. The absorbance corrected fluorescence spectrum may be used to measure fluorescence intensity of a fuel dosed with the quantum photonic marker over a range of wavelengths of light following an absorbance correction method. Absorbance correction may mitigate or correct the effect of an excitation laser absorption and/or a re-absorption of fluorescence emission by a liquid sample. Any suitable absorbance correction method may be employed as would be appreciated by one of ordinary skill in the art upon viewing this disclosure. Axis 1702 represents wavelengths of light for a fluorescence spectra and axis 1704 represents fluorescence intensity levels. The fluorescence spectra comprises wavelengths of light from about 650 nm to about 800 nm. The quantum photonic marker and fuels correspond with the quantum photonic and fuels used to generate graph 1500 in FIG. 15. Fuel 1708 corresponds with a low absorbing fuel such as fuel 1508 in FIG. 15. Fuel 1706 corresponds with a high absorbing fuel such as fuel 1506 in FIG. 15.

While several embodiments have been provided in the present disclosure, it should be understood that the disclosed systems and methods might be embodied in many other specific forms without departing from the spirit or scope of the present disclosure. The present examples are to be considered as illustrative and not restrictive, and the intention is not to be limited to the details given herein. For example, the various elements or components may be combined or integrated in another system or certain features may be omitted, or not implemented.

In addition, techniques, systems, subsystems, and methods described and illustrated in the various embodiments as discrete or separate may be combined or integrated with other systems, modules, techniques, or methods without departing from the scope of the present disclosure. Other items shown or discussed as coupled or directly coupled or communicating with each other may be indirectly coupled or communicating through some interface, device, or intermediate component whether electrically, mechanically, or otherwise. Other examples of changes, substitutions, and alterations are ascertainable by one skilled in the art and could be made without departing from the spirit and scope disclosed herein.

What is claimed is:

1. A liquid sample analysis method comprising;
providing an excitation light and a broadband light to a liquid sample;
obtaining, by a fluorescence spectrometer, measured emission pre-spectrum from the liquid sample;
storing the measured emission pre-spectrum in a memory;
determining a peak of the measured emission pre-spectrum, wherein the peak comprises a first intensity;
adjusting, when the first intensity is outside a desired range, an integration time to produce a measured emission spectrum of intensity versus wavelength;
generating a predicted concentration of a fluorescent tagging compound in the liquid sample using the measured emission spectrum;
comparing the predicted concentration of the fluorescent tagging compound in the liquid sample to a preset concentration of the fluorescent tagging compound in the liquid sample; and
determining whether the measured emission spectrum is a member of a class for a sub-model based on spectral fitness metrics, wherein the spectral fitness metrics comprise a spectrum fit based on the measured emission spectrum, a matrix of spectrum weights, and a matrix of spectrum loadings.

2. The method of claim 1, wherein generating the predicted concentration of the fluorescent tagging in the liquid sample comprises performing a multivariate analysis.

3. The method of claim 2, wherein performing the multivariate analysis comprises:
determining whether the measured emission spectrum is the member of the class for the sub-model based on spectral similarity metrics; and
classifying the measured emission spectrum.

4. The method of claim 1, wherein generating the predicted concentration of the fluorescent tagging in the liquid sample comprises performing a background subtraction analysis.

5. The method of claim 1, further comprising:
determining an absorption of a laser based on a second intensity of the excitation light, and
adjusting the measured emission spectrum based on the absorption of the laser.

6. The method of claim 1, further comprising:
determining an absorbance of a broadband light source based on the broadband light, and
adjusting the measured emission spectrum based on the absorbance of the broadband light source.

7. The method of claim 1, further comprising determining whether the liquid sample is adulterated based on the comparing of the predicted concentration of the fluorescent tagging compound in the liquid sample to the preset concentration of the fluorescent tagging compound in the liquid sample.

8. The method of claim 1, wherein the adjusting comprises:
determining that the first intensity is outside the desired range;
altering the integration time to bring the first intensity into the desired range;
recording a series of spectra using the integration time;
averaging the series to obtain an averaged spectrum; and
dividing intensities at each of a plurality of wavelengths by the integration time to obtain the measured emission spectrum.

9. A liquid sample emission spectrum classification method comprising:
obtaining, by a fluorescence spectrometer, a liquid sample emission pre-spectrum for a liquid sample;
storing the liquid sample emission pre-spectrum in a memory;
determining a peak of the liquid sample emission pre-spectrum, wherein the peak comprises an intensity;
adjusting, when the intensity is outside a desired range, an integration time to produce a liquid sample emission spectrum of intensity versus wavelength;
determining whether the liquid sample emission spectrum is a member of a class for a sub-model based on spectral similarity metrics;
determining whether the liquid sample emission spectrum is the member of the class for the sub-model based on spectral fitness metrics, wherein the spectral fitness metrics comprise a spectrum fit based on the liquid sample emission spectrum, a matrix of spectrum weights, and a matrix of spectrum loadings; and
classifying the liquid sample emission spectrum as in-model. when the liquid sample emission spectrum is a member of the class for the sub-model based on the spectral similarity metrics and the spectral fitness metrics.

10. The method of claim 9, further comprising classifying the liquid sample emission spectrum as out-of-model when the liquid sample emission spectrum is not a member of the class for the sub-model based on the spectral similarity metrics.

11. The method of claim 9, further comprising classifying the liquid sample emission spectrum as out-of-model when the liquid sample emission spectrum is not a member of the class for the sub-model based on the spectral fitness metrics.

12. The method of claim 9, further comprising generating a predicted concentration of a fluorescent tagging compound using the liquid sample emission spectrum and the sub-model.

13. The method of claim 12, further comprising comparing the predicted concentration of the fluorescent tagging compound to a preset concentration of the fluorescent tagging compound.

14. The method of claim 9, further comprising:
obtaining an absorbance spectrum for the liquid sample; and
adjusting the liquid sample emission spectrum based on the absorbance spectrum.

15. The method of claim 9, wherein the sub-model is associated with an inclusive flag or an exclusive flag.

16. The method of claim 9, wherein determining whether the liquid sample emission spectrum is a member of the class for the sub-model based on the spectral similarity metrics comprises comparing the liquid sample emission spectrum to a discriminant function.

17. The method of claim 16, wherein the discriminant function defines a geometric shape in a principle component (PC) space, and wherein comparing the liquid sample emission spectrum to a discriminant function comprises determining a location of the liquid sample emission spectrum relative to the geometric shape.

18. The method of claim 9, wherein determining whether the liquid sample emission spectrum is a member of the class for the sub-model based on the spectral fitness metrics comprises comparing the liquid sample emission spectrum to a scaled sum of square error (SSSE) threshold.

19. A liquid sample analysis method comprising:
obtaining, by a fluorescence spectrometer, a measured emission pre-spectrum for a liquid sample;
storing the measured emission pre-spectrum in a memory;
determining a peak of the measured emission pre-spectrum, wherein the peak comprises an intensity;
adjusting, when the intensity is outside a desired range, an integration time to produce a measured emission spectrum of intensity versus wavelength;
selecting a sub-model for the measured emission spectrum;
determining whether the measured emission spectrum is a member of a class for the sub-model based on spectral fitness metrics, wherein the spectral fitness metrics comprise a spectrum fit based on the measured emission spectrum, a matrix of spectrum weights, and a matrix of spectrum loadings
determining whether the measured emission spectrum is in-model for the sub-model;
determining whether the sub-model is associated with an inclusive flag; and
performing a quantitative analysis on the measured emission spectrum when the measured emission spectrum is in-model for the sub-model and the sub-model is associated with the inclusive flag.

20. The method of claim 19, wherein performing a quantitative analysis comprises performing a multivariate analysis on the measured emission spectrum.

21. The method of claim 19, wherein determining whether the measured emission spectrum is in-model for the sub-model comprises:
   determining whether the measured emission spectrum is the member of the class for the sub-model based on spectral similarity metrics; and
   determining that the measured emission spectrum is in-model for the sub-model when the measured emission spectrum is a member of the class for the sub-model based on the spectral similarity metrics and the spectral fitness metrics.

22. The method of claim 19, further comprising:
   obtaining an absorbance spectrum for the liquid sample; and
   adjusting the measured emission spectrum based on the absorbance spectrum.

\* \* \* \* \*

UNITED STATES PATENT AND TRADEMARK OFFICE
CERTIFICATE OF CORRECTION

PATENT NO. : 9,995,681 B2
APPLICATION NO. : 14/808041
DATED : June 12, 2018
INVENTOR(S) : Jeffrey L. Conroy et al.

Page 1 of 1

It is certified that error appears in the above-identified patent and that said Letters Patent is hereby corrected as shown below:

In the Claims

Claim 2, Column 35, Line 6, replace "fluorescent tagging in" with --fluorescent tagging compound in--.
Claim 4, Column 35, Line 15, replace "fluorescent tagging in" with --fluorescent tagging compound in--.

Signed and Sealed this
Seventh Day of August, 2018

Andrei Iancu
*Director of the United States Patent and Trademark Office*